US006472188B1

(12) United States Patent
Lee et al.

(10) Patent No.: US 6,472,188 B1
(45) Date of Patent: Oct. 29, 2002

(54) METHOD FOR PRODUCING HYDROXYCARBOXYLIC ACIDS BY AUTO-DEGRADATION OF POLYHYDROXYALKANOATES

(75) Inventors: Sang Yup Lee; Fulai Wang; Young Lee, all of Taejon-si (KR)

(73) Assignee: ChiroBio Inc., Taejon (KR)

( * ) Notice: Subject to any disclaimer, the term of this patent is extended or adjusted under 35 U.S.C. 154(b) by 0 days.

(21) Appl. No.: 09/554,948

(22) PCT Filed: Dec. 2, 1998

(86) PCT No.: PCT/KR98/00395

§ 371 (c)(1),
(2), (4) Date: May 22, 2000

(87) PCT Pub. No.: WO99/29889

PCT Pub. Date: Jun. 17, 1999

(30) Foreign Application Priority Data

Dec. 9, 1997 (KR) ............................................. 97-66842

(51) Int. Cl.$^7$ .............................. C12P 7/40; C12N 1/00; C12N 1/20
(52) U.S. Cl. ........................................ 435/136; 435/822
(58) Field of Search .................................. 435/136, 822

(56) References Cited

U.S. PATENT DOCUMENTS 5,107,016 A * 4/1992 Pennetreau .................. 560/179

FOREIGN PATENT DOCUMENTS

JP 9-234091 * 9/1997

OTHER PUBLICATIONS

Doi et al. FEMS Microbiology Review. 1992. 103: 103–108.*
Kim et al. Journal of Microbiology. 1996. vol. 6, No. 6, pp. 425–431.*
Muller et al. Angew. Chem. Int. Ed. Engl. 1993. 32:477–502.*
Valentin et al. Journal of Biotechnilogy. 1997. 58:33–38.*

"A Synthetic Approach to (+)–Thienamycin from Methyl (R)–3–Hydroxybutanoate. A New Entry to (3R 4R)–3–[(R)–1–Hydroxyethyl]–4–Acetoxy–2– Azetidinone". Chiba et al. Chemistry Letters. 1985. pp. 651–656.
"A Facile Entry to 3–(1–Hydroxyethyl)–2–Azetidinones from Methyl (R)–3–Hydroxybut–Anoate Based on the Ester Enolate–Aldimine Condensation", Chiba et al. Chemistry Letters. 1984. pp. 1927–1930.
"Direct Degradation of the Biopolymer Poly [(R)–3–Hydroxybutyric Acid] to (R) –3– Hydroxybutanoic Acid and its Methyl Ester", Seebach et al. Org. Synth. 1992. 71:39–47.

* cited by examiner

Primary Examiner—Sandra E. Saucier
Assistant Examiner—Vera Afremova
(74) Attorney, Agent, or Firm—Bachman & LaPointe, P.C.

(57) ABSTRACT

The present invention provides a method for producing. optically active hydroxycarboxylic acid monomers by auto-degradation of polyhydroxyalkanoates (PHAs). In particular, the present invention provides a method for producing hydroxycarboxylic acid monomers (mostly optically active in (R)-(−)-configuration) comprising the steps of: (a) synthesizing and accumulating PHAs by culturing various microorganisms; and (b) preparing optically active hydroxycarboxylic acids which are monomers of PHAs, by auto-degradation of PHAs by keeping the cultured microorganism in a degradation solution such as water, salt solution, mixture of water and organic solvents, and buffer solution. The present invention also provides a method for the separation of the prepared (R)-(−)-hydroxycarboxylic acids using liquid chromatography (LC) or high performance liquid chromatography (HPLC), and also provides further purification method by removing impurities from the purely separated (R)-(−)-hydroxycarboxylic acids by organic solvent extraction and powder-making process of drying the purified hydroxycarboxylic acids. The present method is economical since hydroxycarboxylic acids can be efficiently produced with high purity and yield by simple process. Also, the present method is environmentally friendly since organic solvents, which are required in large amounts in conventional methods, are used only in minimal amounts in the present invention.

18 Claims, 5 Drawing Sheets

METHOD FOR PRODUCING HYDROXYCARBOXYLIC ACIDS BY AUTO-DEGRADATION OF POLYHYDROXYALKANOATES

FIELD OF THE INVENTION

The present invention relates to a method for producing hydroxycarboxylic acid monomers (mostly optically active in (R)-(−)-configuration) by auto-degradation of polyhydroxyalkanoates (PHAs). In particular, the present invention relates to a method for producing hydroxycarboxylic acid monomers comprising the steps of: (a) synthesizing and accumulating PHAs by culturing various microorganisms; and (b) preparing optically active (R)-(−)-hydroxycarboxylic acids, which are monomers of PHAs, by auto-degradation of PHAs by putting the cells containing PHAs in a degradation solution such as water, salt solution, mixture of water and organic solvents, and buffer solution. The method of the present invention also includes further the separation process for the separation of the prepared (R)-(−)-hydroxycarboxylic acids, if they exist as a mixture of two or more (R)-(−)-hydroxycarboxylic acids, using liquid chromatography (LC) or high performance liquid chromatography (HPLC), and also includes further the purification process for the removal of impurities from the purely-separated (R)-(−)-hydroxycarboxylic acids by organic solvent extraction and the powder-making process of the purified (R)-(−)-hydroxycarboxylic acids.

BACKGROUND OF THE INVENTION (R)-(−)-3-hydroxycarboxylic acid can be widely used as a chiral precursor for several reasons as follows: it contains two functional groups, hydroxyl-group and carboxyl-group; the functional groups are convenient to modify; and a new chiral center can be introduced. And (R)-(−)-3-hydroxycarboxylic acid can be widely used as a precursor for synthesizing antibiotics, vitamins, aromatics, pheromones and the like; as a material for developing non-peptide ligand used in drug design; as a precursor for developing new drug; and especially as a precursor of carbapenem antibiotics, which has recently been drawing much attention to replace β-lactam antibiotics such as penicillin (Scott, In: Asymmetric Synthesis, Morrison and Scott, Eds., Academic Press Inc., Orlando, Fla., 1984). In addition, it was reported that (+)-thienamycin could be synthesized from methyl-(R)-(−)-3-hydroxybutyrate (Chiba and Nakai, Chem,. Lett., 651–654, 1985; Seebach and Zuger, Helvetica Chim. Acta, 65: 495–503, 1982)

Presently, (R)-(−)-3-hydroxycarboxylic acid is mainly produced by the following methods: oxidation of aliphatic glycol by fermentation process (Harada and Hirayashi, Agric. Biol. Chem., 32: 1175, 1968); (R)-(−)-β-hydroxylation of carboxylic acid using microorganisms (Hasegawa et al., J. Ferment. Technol., 60: 501, 1982); and hydrogenation of β-diketone using chiral catalyst (Noyori et al., J. Am. Chrem. Soc., 109: 5856, 1987; Brussel et al., WO97/14500A1, 1997).

Polyhydroxyalkanoates (PHAs) are a carbon and/or energy storage material synthesized and accumulated in numerous microorganisms (Anderson and Dawes, Microbiol. Rev., 54: 450–472, 1990). More than 120 kinds of monomers have been found to be the constituents of PHAs, which can vary depending on the cultured microorganisms, chemical substrate or cosubstrate used, and culture conditions (Lee, Biotechnol. Bioeng., 49: 1–14, 1996; Steinbuchel and Valentin, FEMS Microbiol. Lett., 128: 219–228, 1995). Optically-pure (R)-(−)-hydroxycarboxylic acids may be easily prepared by degrading biosynthesized PHAs since the monomer units of biosynthesized PHAs are composed of monomers all in (R)-(−)-configuration, if the monomer has chiral center on the carbon possessing hydroxyl group, due to the optical specificity of biosynthetic enzymes. A method for producing (R)-(−)-3-hydroxyburyric acid and (R)-(−)-3-hydroxyvaleric acid from poly-(R)-(−)-3-hydroxybutyrate (PHB) or poly-(R)-(−)-3-hydroxybutyrate-co-(R)-(−)-3-hydroxyvalerate (PHB/V) by chemical degradation was reported (Seebach et al., Org. Synth., 71: 39–47, 1992; Seebach and Zuger, Helvetica Chim. Acta, 65: 495–503, 1982; Pennetreau, US005107016A, 1992; Pennetreau, EP0377260A1, 1989).

However, in the above method of producing (R)-(−)-3-hydroxybutyric acid and (R)-(−)-3-hydroxyvaleric acid by chemical degradation, organic solvents were used in large amounts, and the production efficiency was rather low due to complicated processes. Therefore, a new method for producing optically active hydroxycarboxylic acid, which can solve the above problem, is highly required in this field.

Very recently, a method for producing (R)-(−)-3-hydroxybutyric acid by microorganisms has been reported (Akira and Tatsuhiko, JP9-234091, 1997). This method was based on the simple obvious assumption that some microorganisms which accumulate poly-(R)-(−)-3-hydroxybutyrate (PHB) would also be able to produce its monomer, (R)-(−)-3-hydroxybutyric acid. They screened for micrcorgarisms that produce (R)-(−)-3-hydroxybutyric acid, and found that Pseudomonas sp., Burkholderia sp. and Alcaligenes eutrophus were able to produce (R)-(−)-3-hydroxybutyric acid. Here, it should be noted that Alcaligenes eutrophus has recently been renamed as Ralstonia eutropha, and therefore, does not belong to the family of Alcaligenes anymore (Yabuuchi et al., Microbiol. Immunol., 39: 897–904, 1995). In the above method, microorganisms were cultivated for several days (4–7 days), and then transferred to potassium phosphate buffer solution for the production of (R)-(−)-3-hydroxybutyric acid. The monomer yields were very low at 2–8%. Furthermore, production of only (R)-(−)-3-hydroxybutyric acid, but not other (R)-(−)-hydroxycarboxylic acids, was reported. Since the monomer yields were extremely low and it took several days resulting in low productivity (defined as gram product produced per unit volume per unit time), the above method is not suitable for industrial applications.

PHAs are synthesized and accumulated inside the cells usually when one of the growth factors, such as nitrogen, phosphorus, oxygen, potassium and sulfur, is limiting while carbon source is in excess (Anderson and Dawes, Microbiol. Rev., 54: 450–472, 1990). Thus, if the limiting growth factor is supplied again, cells degrade the accumulated PHAs and grow.

All microorganisms that synthesize PHAs contain intracellular PHA depolymerase as well as PHA biosynthesis enzymes. Intracellular PHA depolymerase is known to exist in two states, soluble form and attached form to PHA granules (Merrick and Dourdoroff, *J. Bacteriol.*, 88: 60–71, 1964; Merrick et al., *J. Bacteriol.*, 89: 234–239, 1965; Merrick and Yu, *Biochem.*, 5: 3563–3568, 1966; Griebel et al., *Biochemn.*, 7: 3676–3681, 1968; Griebel and Merrick, *J. Bacteriol.*, 108: 782–789, 1971; Anderson and Dawes, *Microbiol. Rev.*, 54: 450–472, 1990). Merrick and Doudoroff (*J. Bacteriol.* 88: 60–71, 1964) showed that native poly-(R)-(−)-3-hydroxybutyrate (PHB) granules, but not the solvent extracted PHB granules, could be depolymerized by an intracellular depolymerase system. They demonstrated that the PHB granules accumulated in *Bacillus megaterium* could be hydrolyzed to (R)-(−)-3-hydroxybutyric acid by a crude enzyme fraction of PHB-depleted cells of *Rhodospirillum rubrum*. Furthermore, Hippe and Schlegel (*Arch. Mikrobiol.* 56: 278–299, 1967) reported that the soluble depolymerase from Alcaligenes (*Hydrogenomonas*) spp. could degrade native PHB to give (R)-(−)-3-hydroxybutyric acid. These early studies clearly demonstrated that cells possess intracellular PHA depolymerases, and can degrade PHA into monomers. However, isolation of native (amorphous) PHA granules is not only complicated but also expensive in large scale. Furthermore, isolation of intracellular depolymerase for the depolymerization of PHAs is also cumbersome and expensive. If crude cell extract containing intracellular PHA depolymerase is used for degradation of PHAs into monomers, there is a significant problem of product purification due to the contamination by the components in the crude cell extracts. Another problem that hinders the production of monomers by degradation of PHAs by employing cells is that the degraded products, the monomers of PHAs, are further metabolized by the cells. Therefore, it is imoossible to produce monomers by degradation of PHAs unless the metabolic pathways that further metabolize hydroxycarboxylic acid monomers are made to be inactive or blocked. The present invention is based on the assumption that it may be possible to make the metabolic pathways degrading the hydroxycarboxylic acid monomers inactive while maintaining the activity of the intracellular PHA depolymerases by controlling the environmental factors. This idea is clearly different from the method of Akira and Tatsuhiko (JP9-234091, 1997) in that the intracellular PHA depolymerase system is to be utilized for the production of (R)-(−)-hydroxycarboxylic acid monomers in the present invention, while Akira and Tatsuhiko's method is based on the ability of 3 newly isolated microorganisms (Pseudomonas sp., Burkholderia sp. *Rlastonia eutropha* (formerly known as *Alcaligenes eutrophus*; Yabuuchi et al., *Microbiol. Immunol.*, 39: 897–904, 1995)) that are able to produce (R)-(−)-3-hydroxybutyric acid. And, therefore, the present invention begins from the assumption that the synthesized PHAs may be auto-degraded from the intact cells and the monomers can be released into the extracellular environment by controlling the environmental conditions. Therefore, the present invention provides methods to produce various optically active (R)-(−)-hydroxycarboxylic acid monomers efficiently and economically with high yields.

SUMMARY OF THE INVENTION

The present inventors have successfully developed a new method for producing optically active hydroxycarboxylic acid monomers from PHAs accumulated in microorganism. The method of the present invention comprises the steps of: (a) synthesizing and accumulating PHAs by culturing various microorganisms; and (b) preparing hydroxycarboxylic acids, which are monomers of PHAs (mostly optically active in (R)-(−)-configuration) by auto-degradation of PHAs by keeping the cultured microorganism in a degradation solution such as water, salt solution, mixture of water and organic solvents, and buffer solution. The present method involves separation process of the prepared (R)-(−)-hydroxycarboxylic acids, using liquid chromatography (LC) or high performance liquid chromatography (HPLC), and also involves purification process of removing impurities from the purely-separated (R)-(−)-hydroxycarboxylic acids by organic solvent extraction and powder-making process of drying the purified (R)-(−)-hydroxycarboxylic acids.

Finally, the object of the present invention is to provide a new method for producing various optically active (R)-(−)-hydroxycarboxylic acid monomers with high yields comprising the steps of: (a) synthesizing and accumulating PHAs by culturing various microorganisms, including recombinant strains which can accumulate and intracellularly degrade PHAs; and (b) preparing optically active (R)-(−)-hydroxycarboxylic acid monomers by auto-degradation of PHAs.

The object of the present Invention is also to provide a method for producing (R)-(−)-hydroxycarboxylic acid monomers further comprising the steps of separating the prepared (R)-(−)-hydroxycarboxylic acid monomers, using liquid chromatography (LC) or high performance liquid chromatography (HPLC).

The object of the present invention is also to provide a method for producing final (R)-(−)-hydroxycarboxylic acids powder product further comprising the steps of purifying the purely-separated (R)-(−)-hydroxycarboxylic acids by organic solvent extraction; and making powders of the purified (R)-(−)-hydroxycarboxylic acids by drying.

DETAILED DESCRIPTION OF THE INVENTION

Figure 1:
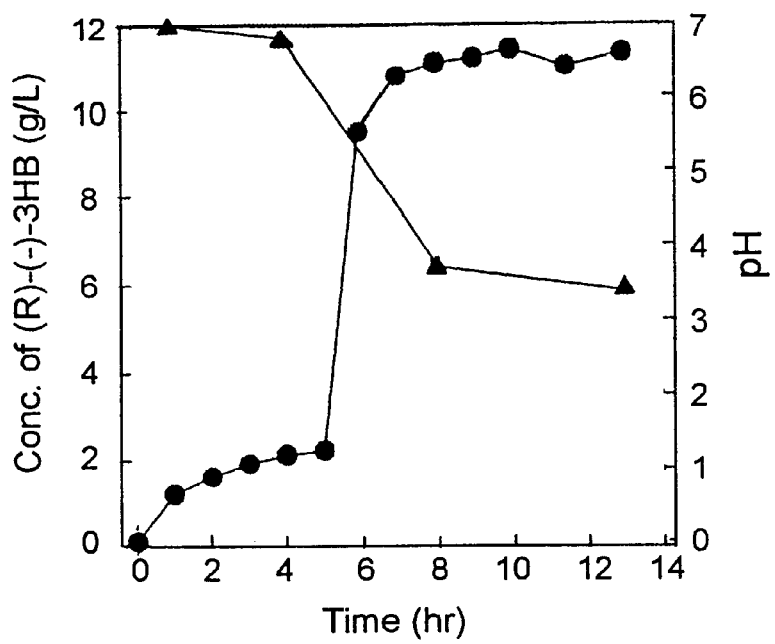
FIG. 1 shows the time profiles of released (R)-(−)-3-hydroxybutyric acid concentration (-●-) and pH of degradation solution (-▲-) during auto-degradation of PHB accumulated in *Alcallgenes latus* without pH control (the initial pH was 7.0).

In the present invention, PHAs are synthesized and accumulated by culturing various microorganisms and a wide range of optically active (R)-(−)-hydroxycarboxylic acid monomers are prepared with high yields by auto-degradation of the PHAs by keeping the microorganism in a degradation solution such as water, salt solution, mixture of water and organic solvents, and buffer solution, which is adjusted to proper pH. Then the prepared (R)-(−)-hydroxycarboxylic acids, if they exist as a mixture of two or more (R)-(−)-hydroxycarboxylic acids, are separated using LC or HPLC. Various kinds of chromatography or ion exchange columns, which are capable of separating organic acids, can be used in LC or HPLC.

In the above, the microorganism can be any wild type, mutant, or recombinant microorganism that accumulate PHAs and possess intracellular depolymerase activity (Doi, Microbial Dolyesters, VCH, New York, 1990; Steinbuchel, In: Biomaterials, Byrom, Eds., MacMillan Publishers, Busings,toke, 1991; Lee, Biotechnol. Bioeng., 49: 1–14, 1996), and may be one selected from the group consisting of microorganisms of the genus Achromobacter including Achromobacter sp., *Achromobacter xylosoxidans* and the like; microorganisms of the genus Acidovorax including *Acidovorax delafieldii, Acidovorax facilis* and the like; microorganisms of the genus Acinetobacter including *Acinetobacter calcoaceticus, Acinetobacter lwoffii* and the like; Actinobacillus sp.; Actinomyces sp.; *Aeromonas caviae*; microorganisms of the genus Alcaligenes including *Alcaligenes aestus, Alcaligenes denitrificans, Alcaligenes faecalis, Alcaligenes latus, Alcaligenes pacificus, Alcaligenes paradoxus, Alcaligenes venustus* and the like; *Alteromonas macleodii*; microorganisms of the genus Amoebobacter including *Amoebobacter roseu, Amoebobacter pendens* and the like; Aphanocapsa sp.; Aphanothece sp.; *Aquaspirillum autotrophicum; Azorhizobium caulinodans*; microorganisms of the genus Azospirillum including *Azospirillum brasilense, Azospirillum lipoferum* and the like; microorganisms of the genus Azotobacter including *Azotobacter agilis, Azotobacter beijerinckii, Azotobacter chroococcum, Azotobacter macrocytogenes, Azotobacter salinestris, Azotobacter vinelandii* and the like; microorganisms of the genus Bacillus including *Bacillus anthracis, Bacillus cereus, Bacillus megaterium, Bacillus subtlis, Bacillus thuringiensis* and the like; microorganisms of the genus Beggiatoa including *Beggiatoa alba* and the like; microorganisms of the genus Beijerinckia including *Beijerinckia fluminensis, Beijerinckia mobilis* and the like; microorganisms of the genus Beneckea including *Beneckea nereida, Beneckea pelagia* and the like; *Bordetella pertussis; Bradyrhizobium japonicum; Caryophanon latum*; microorganisms of the genus Caulobacter including *Caulobacter bacteroides, Caulobacter crescentus* and the like; *Chloroflexus aurantiacus*; microorganisms of the genus Chlorogloea including *Chlorogloea fritschii* and the like; microorganisms of the genus Chrornatium including *Chromatium minutissimum, Chrornatium okenii, Chromatium purpuratum, Chromatium tepidum, Chromatium vinosum* and the like; microorganisms of the genus Chromobacterium including *Chromobacterium violaceum* and the like; microorganisms of the genus Clostridium including *Clostridiurn botulinum, Clostridium sphenoides* and the like; microorganisms of the genus Comamonas including *Comamonas acidovorans, Comarnonas testosteroni* and the like; microorganisms of the genus Corynebacterium including *Corynebacterium autotrophicum, Corynebacterium hydrocarbooxydans* and the like; microorganisms of the genus Derxia including *Derxia gummosa* and the like; *Desulfococcus multivorans*; microorganisms of the genus Desulfonema including *Desulfonema limicola, Desulfonema magnum* and the like; *Desulfosarcina variabilis*; microorganisms of the genus Desulfovibrio including *Desulfovibrio carbinolicus, Desulfovibrio sapovorans* and the like; microorganisms of the genus Ectothiorhodospira including *Ectothiorhodospira halochloris, Ectothiorhodospira mobilis, Ectothiorhodospira shaposhnikovii, Ectothiorhodospira vacuolata* and the like; *Ferrobacillus ferrooxidans*; Flavobacterium sp.; *Haemophilus influenzae*; microorganisms of the genus Halobacterium including *Halobacterium gibbonsii, Halobacterium volcanii* and the like; *Haloferax mediterranei; Hydroclathratus clathratus; Hydrogenomonas facilis*; microorganisms of the genus Hvdrogenophaga including *Hydrogenophaga flava, Hydrogenophaga pseudoflava, Hydrogenophaga taeniospiralis* and the like; microorganisms of the genus Hyphomicrobium including *Hyphomicrobium vulgare, Hyphomicrobium zavarzinii* and the like; *Ilyobacter delafieldii; Labrys monachus*; microorganisms of the genus Lactobacillus including *Lactobacillus brevis, Lactobacillus bulgricys, Lactobacillus casei* and the like; microorganisms of the genus Lactococcus including *Lactococcus cremoris, Lactococcus lactis* and the like; *Lamprocystis roseopersicina; Lampropedla hyalina; Legionella* sp.; *Leptothrix discophorus*; microorganisms of the genus Methylobacterium including *Methylobacterium extorquens, Methylobacterium organophilum, Methylobacterium rhodesianum* and the like; *Methylococcus thermophilus; Methylocystis parvus; Methylomonas methanica*; microorganisms of the genus Methylosinus including *Methylosinus sporium, Methylosinus trichosporium* and the like; *Methylovibrio soehngenii*; microorganisms of the genus Micrococcus including *Micrococcus denitrificans, Micrococcus halodenitrificans* and the like; microorganisms of the genus Microcoleus; microorganisms of the genus Microcystis; microorganisms of the genus Moraxella; microorganisms of the genus Mycobacterium including *Mycobacterium album, Mycobacterium vaccae* and the like; *Mycoplana rubra*; microorganisms of the genus Nitrobacter including *Nitrobacter agilis, Nitrobacter winogradskyi* and the like; microorganisms of the genus Nitrococcus; microorganisms of the genus Nocardia including *Nocardia alba, Nocardia asteroides, Nocardia brasiliensis, Nocardia corallina, Nocardia petroleophila* and the like; *Oscillatoria limosa; Paracoccus dentrificans; Pediococcus halopnilus; Penicillium cyclopium*; microorganisms of the genus Photobacterium including *Photobacterium mandapamensis, Photobacterium phosphoreum* and the like; *Physarum polycephalum; Protomonas extorquens*; microorganisms of the genus Pseudomonas including *Pseudomonas aeruginosa, Pseudomonas alcaligenes, Pseudomonas asplenii, Pseudomonas butanovora, Pseudomonas cepacia, Pseudomonas citronellolis, Pseudomonas coronafaciens, Pseudomonas dacunhae, Pseudomonas denitrificans, Pseudomonas diminuta, Pseudomonas echinoides, Pseudomonas fluorescens, Pseudomonas glathei, Pseudomonas indigofera, Pseudomonas lemonnieri, Pseudomonas mallei, Pseudomonas marina, Pseudomonas mendocina, Pseudomonas mixta, Pseudomonas oleovorans, Pseudomonas oxalaticus, Pseudomonas pseudoalcaligenes, Pseudomonas pseudoflava, Pseudomonas putida, Pseudomonas resinovorans, Pseudomonas saccharophila, Pseudomonas stutzeri, Pseudomonas syringae, Pseudomonas thermophilus, Pseudomonas viridiflava* and the like; microorganisms of the genus Ralstonia including *Ralstonia eutropha* (formerly known as *Alcaligenes eutrophus*; Yabuuchi et al., *Microbiol. Immunol.*, 39: 897–904, 1995); microorganisms of the genus Rhizobium including *Rhizobium galega, Rhizobium hedysarum, Rhizobium leguminosarum, Rhizobium lupini, Rhizobium meliloti, Rhizobium phaseoli, Rhizobium trifoli* and the like; microorganisms of the genus Rhodobacillus; microorganisms of the genus Rhodobacter including *Rhodobacter capsulatus, Rhodobacter sphaeroides* and the like; microorganisms of the genus Rhodococcus including *Rhodococcus opacus, Rhodococcus rhodochrous, Rhodococcus ruber* and the like; microorganisms of the cenus Rhodocycius including *Rhodocyclus gelatinosus, Rhodocyclus tenuis* and the like; *Rhodomicrobium vannielii*; microorganisms of the genus Rhodopseudomonas including *Rhodopseudomonas acidophila, Rhodopseudomonas capsulata, Rhodopseudomonas palustris* and the like; microorganisms of the genus Rhodospirillum including *Rhodospirillum molischianum, Rhodospirillum rubrum* and the like; *Sphaerotilus natans; Sphingomonas paucimobilis*; microorganisms of the genus Spirillum including *Spirillum itersonii, Spirillum lipoferum, Spirillum serpens* and the like; microorganisms of the genus Spirulina including *Spirulina jenneri, Spirulina maxima, Spirulina platensis, Spirulina subsalsa* and the like; microorganisms of the genus Staphylococcus including *Staphylococcus aureus, Staphylococcus epidermidis, Staphylococcus xylosus* and the like; microorganisms of the genus Stella including *Stella humosa, Stella vacuolata* and the like; *Streptococcus thermophilus*; microorganisms of the genus Streptomyces including *Streptomyces antibioticus, Streptomyces coelicolor, Streptomyces venezuelae* and the like; microorganisms of the genus Synechococcus; *Syntrophomonas wolfei*; microorganisms of the genus Thiobacillus including *Thiobacillus acidophil us, Thiobaclilus versutus* and the like; microorganisms of the genus Thiocapsa including *Thiocapsa pfennigii* and the like; *Thiocystis violacea*; microorganisms of the genus Thiodictyon; *Thiosphaera pantotropha; Trichodesmimum thiebautii; Vibrio parahaemolyticus; Xanthobacter autotrophicus; Xanthomonas maltophilia*; and microorganisms of the genus Zoogloea including *Zoogloea ramigera*.

(R)-(−)-hydroxycarboxylic acid monomers, which are prepared by auto-degradation of PHAs synthesized by various microorganisms, may be one or more of the followings, and any other monomers which can be incorporated into PHAs accordinc to a carbon source or chemical compound used during the cultivation of microorganisms (Lee, *Biotechnol. Bioeng.*, 49: 1–14, 1996; Steinbuchel and Valentin, *FEMS Microbiol. Lett.*, 128: 219–228, 1995 and references cited therein): (R)-(−)-3-hydroxybutyric acid, (R)-(−)-3-hydroxyvaleric acid, 4-hydroxybutyric acid, medium chain (R)-(−)-3-hydroxycarboxylic acid monomers of $C_6$ to $C_{14}$ ((R)-(−)-3-hydroxyhexanoic acid, (R)-(−)-3-hydroxyheptanoic acid, (R)-(−)-3-hydroxyoctanoic acid, (R)-(−)-3-hydroxynonanoic acid (R)-(−)-3-hydroxydecanoic acid, (R)-(−)-3-hydroxyundecanoic acid, (R)-(−)-3-hydroxydodecanoic acid and (R)-(−)-3-hydroxytetradecanoic acid), 3-hydroxypropionic acid, (R)-(−)-3-hydroxyhexadecanoic acid, (R)-(−)-4-hydroxyvaleric acid, (R)-(−)-4-hydroxyhexanoic acid, (R)-(−)-4-hydroxyheptanoic acid, (R)-(−)-4-hydroxyoctanoic acid, (R)-(−)-4-hydroxydecanoic acid, 5-hydroxyvaleric acid, (R)-(−)-5-hydroxyhexanoic acid, (R)-(−)-6-hydroxydodecanoic acid, (R)-(−)-3-hydroxy-4-pentenoic acid (R)-(−)-3-hydroxy-4-trans-hexenoic acid, (R)-(−)-3-hydroxy-4-cis-hexenoic acid, (R)-(−)-3-hydroxy-5-hexenoic acid (R)-(−)-3-hydroxy-6-trans-octenoic acid, (R)-(−)-3-hydroxy-6-cis-octenoic acid, (R)-(−)-3-hydroxy-7-octenoic acid, (R)-(−)-3-hydroxy-8-nonenoic acid, (R)-(−)-3-hydroxy-9-decenoic acid, (R)-(−)-3-hydroxy-5-cis-dodecenoic acid, (R)-(−)-3-hydroxy-6-cis-dodecenoic acid, (R)-(−)-3-hydroxy-5-cis-tetradenoic acid, (R)-(−)-3-hydroxy-7-cis-tetradecenoic acid, (R)-(−)-3-hydroxy-5,8-cis-cis-tetradecenoic acid, (R)-(−)-3-hydroxy-4-methylvaleric acid, (R)-(−)-3-hydroxy-4-methylhexanoic acid, (R)-(−)-3-hydroxy-5-methylhexanoic acid, (R)-(−)-3-hydroxy-6-methylheptanoic acid, (R)-(−)-3-hydroxy-4-methyloctanoic acid (R)-(−)-3-hydroxy-5-methyloctanoic acid, (R)-(−)-3-hydroxy-6-methyloctanoic acid, (R)-(−)-3-hydroxy-7-methyloctanoic acid, (R)-(−)-3-hydroxy-6-methylnonanoic acid, (R)-(−)-3-hydroxy-7-methylnonanoic acid (R)-(−)-3-hydroxy-8-methylnonanoic acid, (R)-(−)-3-hydroxy-7-methyldecanoic acid, (R)-(−)-3-hydroxy-9-methyldecanoic acid (R)-(−)-3-hydroxy-7-methyl-6-octenoic acid, malic acid, (R)-(−)-3-hydroxysuccinic acid-methyl ester, (R)-(−)-3-hydroxyadipinic acid-methyl ester, (R)-(−)-3-hydroxysuberic acid-methyl ester, (R)-(−)-3-hydroxyazelaic acid-methyl ester, (R)-(−)-3-hydroxysebacic acid-methyl ester, (R)-(−)-3-hydroxysuberic acid-ethyl ester, (R)-(−)-3-hydroxysebacic acid-ethyl ester, (R)-(−)-3-hydroxypimelic acid-propyl ester, (R)-(−)-3-hydroxysebacic acid-benzyl ester, (R)-(−)-3-hydroxy-8-acetoxyoctanoic acid, (R)-(−)-3-hydroxy-9-acetoxynonanoic acid, phenoxy-(R)-(−)-3-hydroxybutyric acid, phenoxy-(R)-(−)-3-hydroxyvaleric acid, phenoxy-(R)-(−)-3-hydroxyheptanoic acid, phenoxy-(R)-(−)-3-hydroxyoctanoic acid, para-cyanophenoxy-(R)-(−)-3-hydroxybutyric acid, para-cyanophenoxy-(R)-(−)-3- hydroxyvaleric acid, para-cyanophenoxy-(R)-(−)-3-hydroxyhexanoic acid, para-nitrophenoxy-(R)-(−)-3-hydroxyhexanoic acid, (R)-(−)-3-hydroxy-5-phenylvaleric acid, (R)-(−)-3-hydroxy-5-cyclohexylbutyric acid, (R)-(−)-3,12-dihydroxydodecanoic acid, (R)-(−)-3,8-dihydroxy-5-cis-tetradecenoic acid, (R)-(−)-3-hydroxy-4,5-epoxydecanoic acid, (R)-(−)-3-hydroxy-6,7-epoxydodecanoic acid, (R)-(−)-3-hydroxy-8,9-epoxy-5,6-cis-tetradecanoic acid, 7-cyano-(R)-(−)-3-hydroxyheptanoic acid, 9-cyano-(R)-(−)-3-hydroxynonanoic acid, (R)-(−)-3-hydroxy-7-fluoroheptanoic acid, (R)-(−)-3-hydroxy-9-fluorononanoic acid, (R)-(−)-3-hydroxy-6-chlorohexanoic acid, (R)-(−)-3-hydroxy-8-chlorooctanoic acid, (R)-(−)-3-hydroxy-6-bromohexanoic acid, (R)-(−)-3-hydroxy-8-bromooctanoic acid, (R)-(−)-3-hydroxy-11-bromoundecanoic acid, 3-hydroxy-2-butenoic acid, (R)-(−)-6-hydroxy-3-dodecenoic acid, (R)-(−)-3-hydroxy-2-methylbutyric acid, (R)-(−)-3-hydroxy-2-methylvaleric acid and (R)-(−)-3-hydroxy-2,6-dmethyl-5-heptenoic acid.

In the above monomers of PHAs, 3-hydroxypropionic acid, 4-hydroxybutyric acid, 5-hydroxyvaleric acid and 3-hydroxy-2-butenoic acid do not have chiral centers, and thus they do not have optical isomer. The other monomers, which have chiral centers, exist all in (R)-(−)-form.

In the above various monomers, (R)-(−)-3-hydroxybutyric acid, (R)-(−)-3-hydroxybutyric acid/4-hydroxybutyric acid, (R)-(−)-3-hydroxybutyric acid/(R)-(−)-3-hydroxyvaleric acid, (R)-(−)-hydroxycarboxylic acid monomers of $C_6$ to $C_{14}$ and (R)-(−)-3-hydroxy-5-phenylvaleric acid were produced with high yields by auto-degradation as preferable examoles. In more detail, PHB and other PHAs were synthesized by culturing *Alcaligenes latus* DSM 1123, Ralstonia eutropha (formerly known as *Alcaligenes eutrophus*) NCIMB 11599, Ralstonia eutropha (formerly known as *Alcaligenes eutrophus*) H16 ATCC 17699, Corynebacterium sp. SS-15 (Hur et al., Kor. J. Biotechnol. *Bioeng.*, 12: 554–559, 1997), Bacillus sp. SS-19 (Hur et al., *Kor. J. Biotechnol. Bioeng.*, 12: 554–559, 1997), *Methylosinus trichosporium* KCTC 2591, *Rhodospirillum rubrum* KCTC 1372, *Pseudomonas oleovorans* ATCC 29347, *Pseudomonas aeruginosa* PAO1 DSM 1707 or recombinant *Ralstonia eutropha* (Choi and Lee, *Hwahak Konghak*, 35: 684–689, 1997) having the amplified PHA biosynthetic enzyme activities, in a medium, which contains proper carbon source. Then, the cultured cells were collected by centrifugation, dispersed in a degradation solution and auto-degraded under various conditions. Finally, the concentrations of the prepared monomers were determined.

As a result, it was proved that (R)-(−)-hydroxycarboxylic acid monomers could be efficiently prepared by auto-degradation of PHAs, and a proper condition for auto-degradation was determined.

The proper auto-degradation condition for preparing (R)-(−)-hydroxycarboxylic acid is: in case that the microorganism is *Alcaligenes latus* DSM 1123, pH of the degradation solution is 2–11, preferably 2–5, most preferably 3–4, the reaction temperature is 4–55° C., preferably 30–50° C., most preferably 37° C. and the reaction time is 30 minutes-10 hours; in case that the microorganism is *Ralstonia eutropha* NCIMB 11599 (glucose utilizing mutant strain of *Ralstonia eutropha* H16 ATCC 17699), pH of the degradation solution is 2–12, the reaction temperature is 30–40° C. and the reaction time is 20 hours or more; in case that the microorganism is Corynebacterium sp. SS-15, pH of the degradation solution is 5–9, the reaction temperature is 30–40° C. and the reaction time is 2–30 hours; in case that the microorganism is Bacillus sp. SS-19, pH of the degradation solution is 2–12, the reaction temperature is 30–40° C. and the reaction time is 10 hours; in case that the microorganism is *Methylosinus trichosporium* KCTC 2591, pH of the degradation solution is 2–12, the reaction temperature is 30–40° C. and the reaction time is 20 hours or more; in case that the microorganism is *Rhodospirillum rubrum* KCTC 1372, pH of the degradation solution is 2–12, the reaction temperature is 30–40° C. and the reaction time is 20 hours or more; in case that the microorganism is *Ralstonia eutropha* H16 ATCC 17699, pH of the degradation solution is 2–12, the reaction temperature is 30–40° C. and the reaction time is 20 hours or more; and in case that the microorganism is recombinant *Ralstonia eutropha* having the amplified PHA biosynthetic enzyme activities, pH of the degradation solution is 2–12, the reaction temperature is 30–40° C. and the reaction time is 20 hours or more.

The proper auto-degradation condition for preparing (R)-(−)-3-hydroxybutyric acid/4-hydroxybutyric acid is: in case that the microorganism is *Alcaligenes latus* DSM 1123, pH of the degradation solution is lower than 7, preferably 2–5, the reaction temperature is 30–40° C., preferably 37° C. and the reaction time is 30 minutes-10 hours. In addition, the proper condition of auto-degradation for preparing (R)-(−)-3-hydroxybutyric acid/(R)-(−)-3-hydroxyvaleric acid is: in case that the microorganism is *Ralstonia eutropha* NCIMB 11599, pH of the degradation solution is 2–12, the reaction temperature is 30–40° C. and the reaction time is 20 hours or more.

The proper auto-degradation condition for preparing (R)-(−)-hydroxycarboxylic acid monomers of $C_6$ to $C_{14}$ is: in case that the microorganism is *Pseudomonas oleovorans* ATCC 29347 or *Pseudomonas aeruginosa* PAO1 DSM 1707, pH of the degradation solution is 2–12, the reaction temperature is 30–40° C. and the reaction time is 10 hours or more.

The proper auto-degradation condition for preparing (R)-(−)-3-hydroxy-5-phenylvaleric acid is: in case that the microorganism is *Pseudomonas oleovorans* ATCC 29347, pH of the degradation solution is 2–12, the reaction temperature is 30–40° C. and the reaction time is 10 hours or more.

The other monomers can also be prepared simply by employing various microorganisms and carbon sources/chemical compounds (Lee, *Biotechnol. Bioeng.*, 49: 1–14, 1996; Steinbuchel and Valentin, *FEMS Microbiol. Lett.*, 128: 219–228, 1995).

In the present invention, PHAs at high concentration are also auto-degraded to form the corresponding monomers with high concentration and further, the efficiency of producing monomers can be improved by heat-degrading under alkaline condition the residual dimers, which are by-products produced during the auto-degradation of PHAs.

Water, mixture of water and organic solvents or buffer solution with or without various salts may be used as a degradation solution. The difference due to the degradation solution employed is none or negligible, but water is preferable for the easiness of subsequent separation and purification of monomers.

If PHAs to be degraded are copolymers, the products of auto-degradation under the above condition are mixtures of monomers. These monomers can be easily separated by various conventional methods such as ion exchange, electrodialysis, extraction, distillation, liquid chromatography (LC) and high performance liquid chromatography (HPLC), and preferably by LC or HPLC.

The purely separated (R)-(−)-hydroxycarboxylic acids are further purified by conventional method such as organic solvent extraction and powder-made by conventional method such as drying processing. In more detail, strong alkali such as sodium hydroxide or potassium hydroxide is added to the pure (R)-(−)-hydroxycarboxylic acid solution, which is prepared by auto-degradation, and the pH of the solution is adjusted to higher than 9. Then, impurities, which are extracted into organic phase, are removed, and (R)-(−)-hydroxycarboxylic acids remained in water phase are dried to result in final powder product with the purity of 90% or higher.

The present invention is further illustrated by the following examples that are not intended to be in any way limiting the scope of the invention as claimed.

EXAMPLE 1

Preparation of (R)-(−)-3-hydroxybutyric Acid by Auto-degradation of PHB, Which is Synthesized and Accumulated in *Alcaligenes latus*

A proper condition for auto-degradation of PHB synthesized by *Alcaligenes latus* DSM 1123 was determined. Firstly, the microorganism was cultured to accumulate PHB in batch mode in a chemically defined medium shown in Table 1 supplemented with 30 g/L of sucrose under nitrogen limited condition, and the cultured cells were collected by centrifugation. PHB accumulated in the cells was auto-degraded by the method shown below. Then, the concentrations of (R)-(−)-3-hydroxybutyric acid and its dimer produced under various conditions were determined.

Several factors examined during auto-degradation include pH of degradation solution (Table 2), carbon source and stirring (Table 3 and Table 4) and temperature of auto-degradation (Table 5 and Table 6). (R)-(−)-3-hydroxybutyric acid was prepared most efficiently when auto-degradation was carried out at pH 4.0 and 37° C. without stirring (and without oxygen).

As a degradation solution, water and various salt solutions based on a chemically defined medium without carbon source, which is pH-adjusted with various acids hydrochloric acid, sulfuric acid, acetic acid) or alkali (sodium hydroxide, ammonia water), or buffer solution (40 mM phosphate buffer solution, 40 mM acetate buffer solution, 40 mM citrate buffer solution, Tris-HCl buffer solution, MOPS buffer solution), were compared with one another. Differences in the results obtained in various degradation solutions were none or negligible (maximum difference was lower than 3% with respect to yield) as long as pH was the same. Therefore, pH-adjusted water was used as a degradation solution in all examples hereafter considering its beneficial influence on the subsequent separation and purifying processes.

TABLE 1

Composition of a chemically defined medium

| Ingredient | Concentration (g/L) |
|---|---|
| $(NH_4)_2SO_4$ | 1.5 |
| $KH_2PO_4$ | 1.5 |
| $Na_2HPO_4 \cdot 12H_2O$ | 9 |
| $MgSO_4 \cdot 7H_2O$ | 0.5 |
| $CaCl_2 \cdot 2H_2O$ | 0.05 |
| Citric acid | 0.1 |
| $FeSO_4 \cdot 7H_2O$ | 0.06 |
| $H_3BO_4$ | 0.0009 |
| $CoCl_2 \cdot 6H_2O$ | 0.0006 |
| $ZnSO_4 \cdot 7H_2O$ | 0.00009 |
| $MnCl_2 \cdot 4H_2O$ | 0.00009 |
| $(NH_4)_6Mo_7O_{24} \cdot 4H_2O$ | 0.00009 |
| $NiSO_4 \cdot 7H_2O$ | 0.00009 |
| $CuSO_4 \cdot 5H_2O$ | 0.00003 |

TABLE 2

Concentrations of the (R) - (−) -3-hydroxybutyric acid (3HB) and the dimer obtained by varying the pH of degradation solution (initial PHB concentration: 1.07 g/L, reaction temperature: 37° C., reaction time: 30 minutes)

| pH | 2 | 3 | 4 | 5 | 6 | 6.5 | 7 | 8 | 9 | 10 | 11 |
|---|---|---|---|---|---|---|---|---|---|---|---|
| Conc. of 3HB (g/L) | 0.6 | 0.95 | 0.99 | 0.35 | 0.03 | 0.04 | 0.04 | 0.05 | 0.11 | 0.15 | 0.19 |
| Conc. of dimer (g/L) | 0.14 | 0.24 | 0.23 | 0.01 | 0.03 | 0.00 | 0.00 | 0.00 | 0.00 | 0.00 | 0.00 |
| Final yield (mol %) | 58 | 95 | 96 | 31 | 5 | 3 | 3 | 3 | 4 | 12 | 15 |

TABLE 3

Concentrations of the (R)—(—)-3-hydroxybutyric acid (3HB) and the dimer, yield and final pH obtained by varying the sucrose concentration with or without stirring (initial PHB concentration: 1.01 g/L, initial pH: 7.0, reaction temperature: 37° C., reaction time: 8 hours).

| Sucrose conc. (g/L) | Stirring | Conc. Of 3HB (g/L) | Conc. of dimer (g/L) | Yield (mol %) | Final pH |
|---|---|---|---|---|---|
| 20 | Yes | 0.15 | 0 | 1 | 7.0 |

TABLE 3-continued

Concentrations of the (R)—(—)-3-hydroxybutyric acid (3HB) and the dimer, yield and final pH obtained by varying the sucrose concentration with or without stirring (initial PHB concentration: 1.01 g/L, initial pH: 7.0, reaction temperature: 37° C., reaction time: 8 hours).

| Sucrose conc. (g/L) | Stirring | Conc. Of 3HB (g/L) | Conc. of dimer (g/L) | Yield (mol %) | Final pH |
|---|---|---|---|---|---|
| 20 | No | 7.00 | 0.37 | 61 | 3.6 |
| 0 | Yes | 0.04 | 0 | 0 | 7.0 |
| 0 | No | 11.30 | 0.69 | 99 | 3.6 |

TABLE 4

Concentrations of the (R)—(—)-3-hydroxybutyric acid (3HB) and the dimer, and yield obtained by varying the sucrose concentration with or without stirring (initial PHB concentration: 1.07 g/L, initial pH: 4.0, reaction temperature: 37° C., reaction time: 30 minutes).

| Sucrose conc. (g/L) | Stirring | Conc. of 3HB (g/L) | Conc. of dimer (g/L) | Yield (mol %) |
|---|---|---|---|---|
| 20 | Yes | 0.97 | 0.19 | 91 |
| 20 | No | 1.00 | 0.25 | 99 |
| 0 | Yes | 0.95 | 0.22 | 92 |
| 0 | No | 1.01 | 0.20 | 95 |

TABLE 5

Time dependent change of (R) - (-) -3-hydroxybutyric acid (3HB) concentration obtained by varying reaction temperature (initial PHB concentration: 10.9 g/L, initial pH: 7.0)

| Degrading temp. (° C.) | Degradation time (hour) | | | | | | | | | | | | |
|---|---|---|---|---|---|---|---|---|---|---|---|---|---|
| | 0 | 1 | 2 | 3 | 4 | 5 | 6 | 7 | 8 | 9 | 10 | 11.5 | 13 |
| 30 | 0.10 | 0.90 | 1.30 | 1.80 | 1.60 | 1.90 | 2.00 | 2.10 | 7.70 | 9.10 | 10.50 | 11.40 | 10.10 |
| 37 | 0.10 | 1.20 | 1.60 | 1.90 | 2.10 | 2.20 | 9.50 | 10.80 | 11.10 | 11.20 | 11.40 | 11.00 | 11.30 |
| 45 | 0.10 | 1.50 | 2.40 | 2.50 | 2.50 | 2.50 | 2.50 | 2.50 | 2.50 | 2.60 | 2.60 | 2.60 | 2.60 |

TABLE 6

Concentrations of the (R) - (-) -3-hydroxybutyric acid (3HB) and the dimer, and yield obtained at different reaction temperatures (initial PHB concentration: 1.07 g/L, initial pH: 4.0, reaction time: 30 minutes)

| Degrading Temperature (° C.) | 4 | 25 | 30 | 34 | 37 | 45 | 50 | 55 |
|---|---|---|---|---|---|---|---|---|
| Conc. of 3HB (g/L) | 0.09 | 0.49 | 0.77 | 0.98 | 1.01 | 0.92 | 0.78 | 0.23 |
| Conc. Of dimer (g/L) | 0.00 | 0.09 | 0.18 | 0.20 | 0.23 | 0.28 | 0.35 | 0.00 |

In addition, the produced amount of (R)-(−)-3-hydroxybutyric acid according to the pH change was determined with reaction time, which was prepared in a degradation solution adjusted to initial pH of 7.0, to investigate the relationship between the pH of degradation solution and auto-degradation reaction in detail (FIG. 1). As shown in FIG. 1, auto-degradation of PHB was very sensitive to the pH of degradation solution. Auto-degradation hardly occurred at first when the initial pH was adjusted to 7, but the reaction was accelerated with the decrease of pH (pH decreased rapidly and (R)-(−)-3-hydroxybutyric acid was produced rapidly from 6 hour after the beginning of the reaction).

Figure 2:
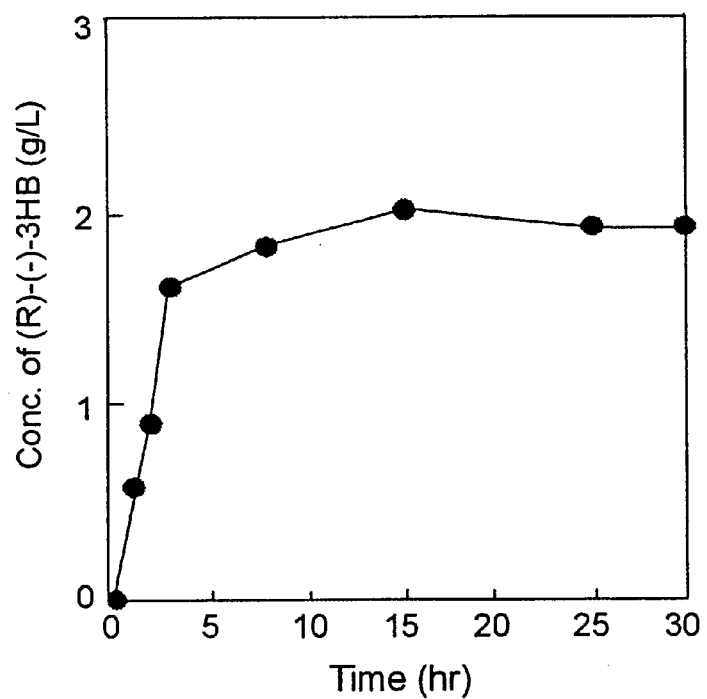
FIG. 2 shows the time profile of released (R)-(−)-3-hydroxybutyric acid concentration during auto-degradation of PHB accumulated in *Alcaligenes latus* with pH control at 7.0.

The similar effect of pH was also observed in auto-degradation reaction performed in a fermenter operated at pH 7 (FIG. 2). That is, cells containing PHB (PHB concentration of 10.1 g/L) were introduced into the fermenter and the reaction was carried out under nitrogen atmosphere. Then auto-degradation was performed at pH 7.0 adjusted by adding 4N NaOH. Only 16% of PHB was degraded even after 30 hours, thus only 2 g/L of (R)-(−)-3-hydroxybutyric acid was obtained.

Therefore, it was proved that the pH of degradation solution is the most important factor for producing (R)-(−)-3-hydroxybutyric acid by auto-degradation of PHB, which is synthesized in *Alcaligenes latus* DSM 1123, and was also proved that low pH condition accelerates auto-degradation of PHB to its monomer (R)-(−)-3-hydroxybutyric acid.

As shown in the above, (R)-(−)-3-hydroxybutyric acid could be efficiently prepared by auto-degradation of PHB under various conditions. Particularly, when the initial pH was 4 and reaction temperature was 34–50° C., the monomer yield of greater than 90% could be obtained within 30 minutes. These results are much better than the previous work reported by Akira and Tatsuhiko (JP9-234091, 1997) who showed that the yield of only 2–8% could be obtained after long time of 6–8 days.

Figure 5:
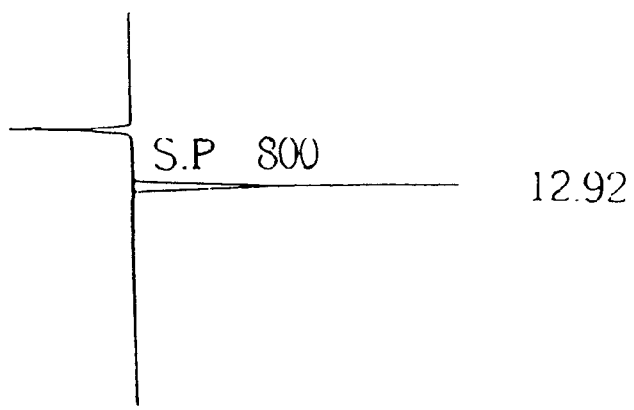
FIG. 5 shows the standard HPLC peak profile of commercial 3-hydroxybutyric acid (Sigma chemical Co., USA).
Figure 7:
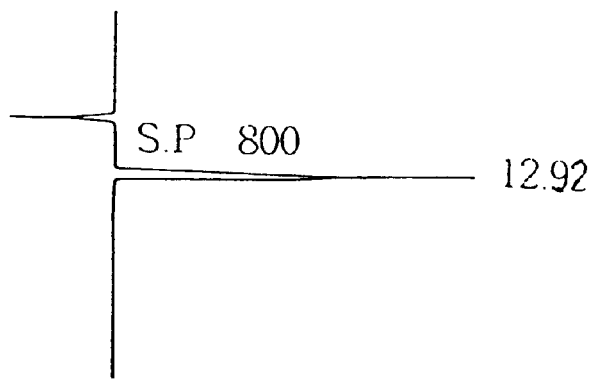
FIG. 7 shows the HPLC peak profile of (R)-(−)-3-hydroxybutyric acid obtained by auto-degradation of PHB accumulated in *Alcaligenes latus*.

In addition, the retention time of the product analyzed by HPLC was compared with that of 3-hydroxybutyric acid racemic mixture purchased from Sigma chemical Co. (USA) to verify that the product was (R)-(−)-3-hydroxybutyric acid (FIG. 5 and FIG. 7). Both samples were detected at 12.9 minute under the same operating condition, which proved that the product was 3-hydroxybutyric acid. This was further confirmed by nuclear magnetic resonance (NMR) analysis (Ref. Example 18).

Similarly, (R)-(−)-3-hydroxybutyric acid could be prepared with the yield of 80–90% by auto-degradation of PHB accumulated in other *Alcaligenes latus* strains including *Alcaligenes latus* DSM 1122 and *Alcaligenes latus* DSM 1124.

EXAMPLE 2

Preparation of Highly-purified (R)-(-)-3-hydroxybutyric Acid by Auto-degradation of PHB at High Concentration, Which is Synthesized and Accumulated in *Alcaligenes latus*, and Degradation of the Dimer Produced as a By-product

EXAMPLE 2-1

As shown in Example 1, PHB of low concentration (10 g/L) could be used to prepare (R)-(-)-3-hydroxybutyric acid with high efficiency and within short time by auto-degradation. However, the use of PHA at high concentration is economically beneficial because production process can be simplified, and the amount of dispensing solvent and the volume of the reaction apparatus can be reduced.

Thus in this example, *Alcaligenes latus* DSM 1123 was cultured in a fed-batch mode and a high concentration of PHB was produced by the method we reported previously (Wang and Lee, Appl. *Environ. Microbiol.*, 63: 3703–3706, 1997). Then, the concentration of PHB was adjusted to a high concentration of 115.3 g/L, and auto-degradation was performed at pH 4, at 37° C. for 1 hour.

As a result, 117.8 g/L of (R)-(-)-3-hydroxybutyric acid (yield of 84%) and 15.2 g/L of the dimer (yield of 12%) were obtained. Thus, it was proved that PHB at high concentration could also be used to prepare (R)-(-)-3-hydroxybutyric acid with high efficiency by auto-degradation.

EXAMPLE 2-2

In Example 2-1, dimers were produced as a reaction by-product due to the incomplete auto-degradation of highly concentrated PHB. In this example, it was attempted to increase the yield of monomer by completely degrading the dimers. That is, 5M solution of sodium hydroxide was added to adjust pH to 11 to the solution containing 117.8 g/L of (R)-(-)-3-hydroxybutyric acid and 15.2 g/L of the dimer, which was prepared in Example 2-1. Then, the solution was poured into a test tube and sealed up. Auto-degradation reaction was performed at 95° C. for 2 hours. As a result, the final concentration of (R)-(-)-3-hydroxybutyric acid increased to 131.9 g/L (yield of 95%) and the dimers were not detected since they were completely degraded into monomers.

Therefore, as shown in Example 2-1 and Example 2-2, (R)-(-)-3-hydroxybutyric acid of high concentration can be prepared efficiently from highly concentrated PHB, and if needed, the yield can be further increased by degrading the dimers under alkaline condition.

EXAMPLE 3

Preparation of Monomers by Auto-degradation of Poly-(R)-(-)-3-hydroxybutyrate-co-4-hydroxybutyrate Copolymer, Which is Synthesized and Accumulated in *Alcaligenes latus*

*Alcaligenes latus* DSM 1123 was cultured in a chemically defined medium containing 10 g/L of sucrose and 3 g/L of 4-hydroxybutyric acid in a flask. Cells accumulated poly-(R)-(-)-3-hydroxybutyrate-co-4-hydroxybutyrate up to 70% of cell dry weight, of which 12 mol % of the polymer was 4-hydroxybutyrate. The cultured cells were collected by centrifugation, dispersed in degradation solution at the copolymer concentration of 21 g/L and then auto-degraded. When auto-degradation was performed at the initial pH of 4, at 37° C. for 4 hour, 13.6 g/L of (R)-(-)-3-hydroxybutyric acid and 2.4 g/L of 4-hydroxybutyric acid were obtained. The yields were 68% and 79%, respectively. Similarly, two monomers could be produced by auto-degradation of poly-(R)-(-)-3-hydroxybutyrate-co-4-hydroxybutyrate produced by growing *Alcaligenes latus* DSM 1123 on sucrose and γ-butyrolactone by the method reported by Hiramitsu et al. (*Biotechnol. Lett.*, 15: 461–464, 1993).

Therefore, (R)-(-)-3-hydroxybutyric acid and 4-hydroxybutyric acid could be efficiently prepared from poly-(R)-(-)-3-hydroxybutyrate-co-4-hydroxybutyrate by auto-degradation and could be purely separated using LC or HPLC (Ref. Example 16).

EXAMPLE 4

Preparation of (R)-(-)-3-hydroxybutyric Acid by Auto-degradation of PHB, Which is Synthesized and Accumulated in *Ralstonia eutropha*

*Ralstonia eutropha* (formerly *Alcaligenes eutrophus*) NCIMB 11599 (Yabuuchi et al., *Microbiol. Immunol.*, 39: 897–904, 1995), a glucose utilizing mutant strain of *Ralstonia eutropha* H16 ATCC 17699, was cultured according to the previously reported method (Kim et al., *Biotechnol. Bioeng.*, 43: 892–898, 1994) under nitrogen limited condition, and cells containing PHB up to 70% of cell dry weight were obtained. Initial concentration of PHB was adjusted to 34 g/L and auto-degradation was performed at 30° C. and at the initial pH of 4.0 or 7.0 for 34 hours. When the initial pH was 4.0, 5.2 g/L of (R)-(-)-3-hydroxybutyric acid and 0.4 g/L of the dimer were produced. When the pH was 7.0, 9.3 g/L of (R)-(-)-3-hydroxybutyric acid and 0.9 g/L of the dimer were produced. The total yields were 14% and 25%, respectively. PHB was not degraded completely in case of *Ralstonla eutropha*, which was different from the case of *Alcaligenes latus*. Furthermore, the optimal condition for monomer production was also different from that of *Alcaligenes latus*. Nonetheless, (R)-(-)-3-hydroxybutyric acid could be prepared by auto-degradation of PHB, which was accumulated in *Raistonia eutropha*, although the producing method using *Ralstonia eutropha* was less efficient than that using *Alcaligenes latus*.

EXAMPLE 5

Preparation of Monomers by Auto-degradation of Poly-(R)-(-)-3-hydroxybutyrate-co-(R)-(-)-3-hydroxyvalerate Copolymer, Which is Synthesized and Accumulated in *Ralstonia eutropha*

*Ralstonia eutropha* NCIMB 11599 was cultured in a medium containing 10 g/L of glucose and 1 g/L of propionic acid, according to the method previously reported (Kim et al., *Enzyme Microbial. Technol.*, 16: 556–561, 1994). Poly-(R)-(-)-3-hydroxybutyrate-co-(R)-(-)-3-hydroxyvalerate (PHB/V) copolymer (containing 8 mol % (R)-(-)-3-hydroxyvalerate) was accumulated to a content of 63% of cell dry weight, which was auto-degraded to produce (R)-(-)-3-hydroxybutyric acid and (R)-(-)-3-hydroxyvaleric acid. Cells were dispersed in water at a copolymer concentration of 27.4 g/L. Auto-degradation reaction was carried out at pH 7 and 30° C. for 35 hours. As a result, 5.8 g/L of (R)-(−)-3-hydroxybutyric acid and 0.6 g/L of (R)-(−)-3-hydroxyvaleric acid were obtained. Therefore, a mixture of (R)-(−)-3-hydroxybutyric acid and (R)-(−)-3-hydroxyvaleric acid can be efficiently prepared from the accumulated PHB/V polymer by auto-degradation of the copolymer, and they can be separated using LC or HPLC (Ref. Example 16).

EXAMPLE 6

Preparation of (R)-(−)-3-hydroxybutyric Acid by Auto-degradation of PHB, Which is Synthesized and Accumulated in Corynebacterium Sp.

Figure 3:
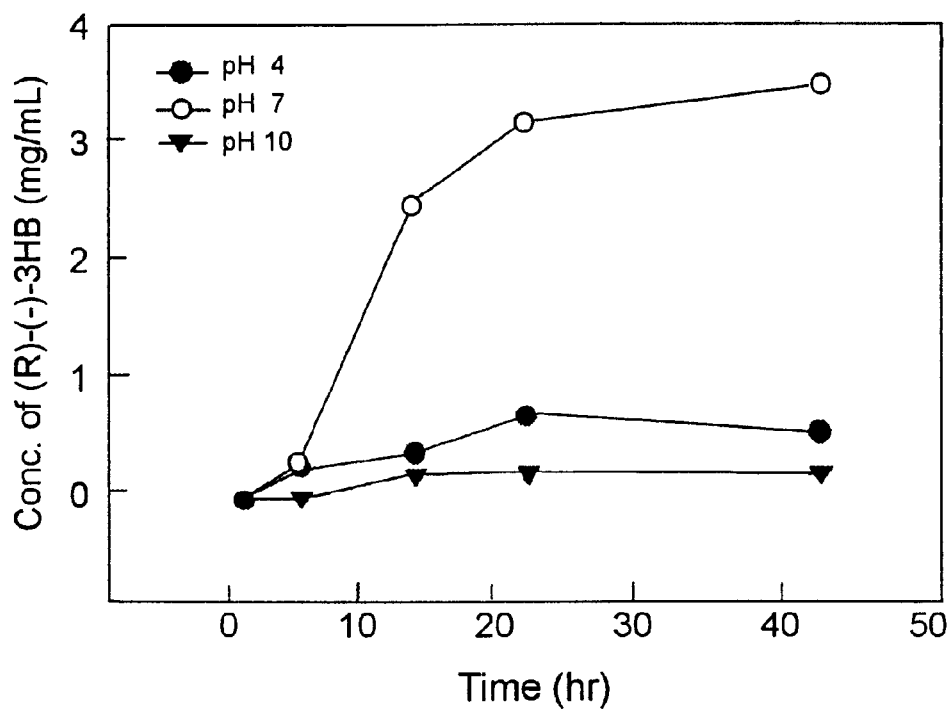
FIG. 3 shows the time profiles of released (R)-(−)-3-hydroxybutyric acid concentration during auto-degradation of PHB accumulated in Corynebacterium sp. when the initial pH was 4.0, 7.0 or 10.0.

Corynebacterium sp. SS-15 [Hur et al., Kor. J. Biotechnol. Bioeng., 12: 554–559, 1997; this strain is available at Department of Chemical Engineering of KAIST (Korea Advanced Institute of Science and Technology in Korea)], which was isolated from a soil, was cultured in a chemically defined medium containing 20 g/L of xylose as a carbon source, in a flask for 3 days. Cells accumulated PHB to 33% of cell dry weight. Cells collected by centrifugation were dispersed in water, which was adjusted to pH 4.0, 7.0 or 10.0, to give the initial PHB concentration of 3.4 g/L and kept at 30° C. The time profiles of (R)-(−)-3-hydroxybutyric acid formation were examined (FIG. 3). When the initial pH was 7.0, the maximum amount of (R)-(−)-3-hydroxybutyric acid obtained was 3.42 g/L at 41 hour after the beginning of the reaction, which resulted in the monomer yield of 83%. Therefore, (R)-(−)-3-hydroxybutyric acid could be efficiently produced by auto-degradation of PHB accumulated in Corynebacterium sp., a Gram+ bacterium.

EXAMPLE 7

Preparation of (R)-(−)-3-hydroxybutyric Acid by Auto-degradation of PHB, Which is Synthesized and Accumulated in Bacillus Sp.

Figure 4:
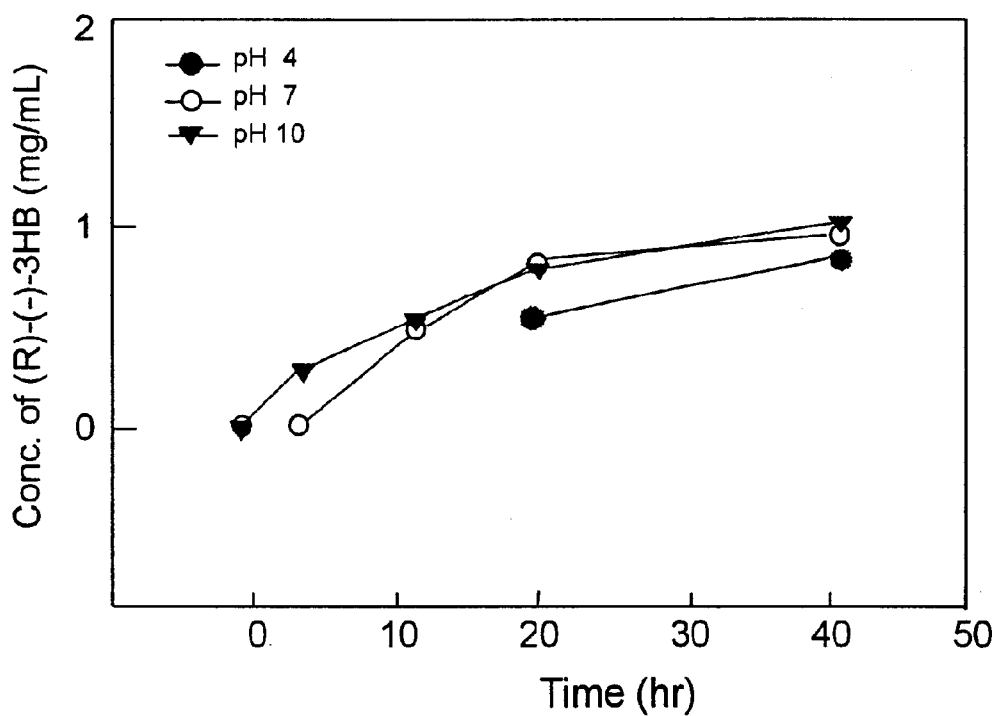
FIG. 4 shows the time profiles of released (R)-(−)-3-hydroxybutyric acid concentration during auto-degradation of PHB accumulated in Bacillus sp. when the initial pH was 4.0, 7.0 or 10.0.

Bacillus sp. SS-19 [Hur et. al., Kor. J. Biotechnol. Bioeng., 12: 554–559, 1997; this strain is available at Department of Chemical Engineering of KAIST (Korea Advanced Institute of Science and Technology in Korea)], which was isolated from a soil, was cultured in a chemically defined medium containing 20 g/L of xylose as a carbon source, in a flask for 3 days. Cells accumulated PHB to a level of 15% of cell dry weight. Cells collected by centrifugation were dispersed in water, which was adjusted to pH 4.0, 7.0 or 10.0, to give the initial PHB concentration of 1.4 g/L and kept at 30° C. The time profiles of (R)-(−)-3-hydroxybutyric acid formation were examined (FIG. 4). When the initial pH was 7.0, the maximum amount of the (R)-(−)-3-hydroxybutyric acid obtained was 0.96 g/L at 20 hour after the beginning of the reaction, which resulted in the yield of 57%. Therefore, (R)-(−)-3-hydroxybutyric acid could be efficiently produced by auto-degradation of PHB accumulated-in Corynebacterium sp., a Gram+ bacterium.

EXAMPLE 8

Preparation of (R)-(−)-3-hydroxybutyric Acid by Auto-degradation of PHB, Which is Synthesized and Accumulated in *Methylosinus trichosporium*

In the above examples, bacteria employed were either aerobic or facultative aerobic. But in this example, *Methylosinus trichosporium* KCTC 2591, which is anaerobic and methane-utilizing bacterium, was cultured by the method of Whang and Park (Whang and Park, Kor. J. Biotechnol. Bioeng., 11: 246–253, 1996) until the cell concentration reached 1.1 g cell dry weight/L, in which the PHB content was 10% of cell dry weight. PHB concentration was adjusted to 10.5 g/L before auto-degradation, then, (R)-(−)-3-hydroxybutyric acid was prepared by auto-degradation of the accumulated PHB, using the same procedure as the above examples (Example 1-7) at pH 4 and 37° C. As a result, 1.15 g/L of (R)-(−)-3-hydroxybutyric acid was obtained after 24 hours, which resulted in the yield of 9%. Therefore, it was demonstrated that (R)-(−)-3-hydroxybutyric acid could also be prepared (even though the efficiency was low) by auto-degradation of PHB, which was accumulated in methane-utilizing anaerobic microorganism.

EXAMPLE 9

Preparation of (R)-(−)-3-hydroxybutyric Acid by Auto-degradation of PHB, Which is Synthesized and Accumulated in Photosynthetic Microorganism *Rhodospirillum rubrum*

*Rhodospirillum rubrum* KCTC 1372, which is anaerobic and photosynthetic bacterium, was cultured by the method of Hashimoto et al. (Hashimoto et al., J. Chem. Eng. Japan, 26: 56–58, 1993). After 140 hours, 1.5 g cell dry weight/L of cells was obtained, in which the PHB content was 16% of cell dry weight. Auto-degradation was performed by the same procedure as the above examples (Example 1-8) at pH 4 and 37° C. using PHB concentrated to 12 g/L. As a result, 1.61 g/L of (R)-(−)-3-hydroxybutyric acid was obtained after 24 hours, which resulted in the yield of 11%. Therefore, it was demonstrated that (R)-(−)-3-hydroxybutyric acid could also be prepared by auto-degradation of PHB, which was accumulated in photosynthetic bacteria.

EXAMPLE 10

Preparation of (R)-(−)-3-hydroxybutyric Acid by Auto-degradation of PHB, Which is Synthesized and Accumulated in *Ralstonia eutropha* H16 (ATCC 17699), Fructose-utilizing Strain

*Ralstonia eutropha* H16 (formerly *Alcaligenes eutrophus* H16) ATCC 17699, which utilizes fructose as a carbon source, was cultured by the method of Hughes et al. (Hughes et al., U.S. Pat. No. 4,433,053, 1984). After 70 hours, cell concentration and PHB content reached 42 g cell dry weight/L and 65%, respectively. Auto-degradation was performed at pH 7 and 30° C. using PHB concentrated to 42 g/L. As a result, 11.7 g/L of (R)-(−)-3-hydroxybutyric acid was obtained after 36 hours, which resulted in the yield of 23%. Therefore, it was proved that (R)-(−)-3-hydroxybutyric acid could also be prepared by auto-degradation of PHB, which was accumulated by culturing the wild type *Ralstonia eutropha* utilizing fructose as a carbon source.

EXAMPLE 11

Preparation of Optically Active Medium Chain Length Hydroxycarboxylic Acids by Auto-degradation of PHAs, Which are Synthesized and Accumulated in *Pseudomonas oleovorans*

It was reported that PHAs, which consist of medium chain length hydroxycarboxylic acid (HA) monomers of $C_6$ to $C_{14}$, can be synthesized and accumulated in *Pseudomonas oleovorans* when cultured on alkanoates, alcohols, alkanols, alkanes or alkenes as carbon sources, and the kinds or the composition of the monomers in the PHA polymer can vary depending on the carbon source employed (Brandl et al., *Appl. Environ. MIcrobiol.*, 54: 1977–1982, 1988; Steinbuchel, In: Biomaterials, Byrom, Eds., MacMillan Publishers, Busingstoke, 1991; Lee, *Biotechnol. Bioeng.*, 49: 1–14, 1996).

For example, if hexanoic acid is used as a carbon source, the synthesized PHA consists of 3-hydroxyhexanoic acid ($C_6$); 3-hydroxyheptanoic acid ($C_7$); 3-hydroxyoctanoic acid ($C_8$); and 3-hydroxydecanoic acid ($C_{10}$), all in (R)-(–) configuration. 3-hydroxyhexanoic acid is the major monomer among the above, being about 82 mol %. The fraction of 3-hydroxyoctanoic acid is 17 mol % and the fraction of 3-hydroxyheptanoic acid and 3-hydroxydecanoic acid is as little as 1 mol %.

If heptanoic acid is used as a carbon source, the synthesized PHA consists of six kinds of monomers (3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid), which are C6 to $C_{10}$ compounds, all in (R)-(–) configuration. (R)-(–)-3-hydroxyheptanoic acid is the major monomer among the above, being 94 mol %.

If octanoic acid is used as a carbon source, the synthesized PHA consists of even numbered carbon compounds, namely (R)-(–)-3-hydroxyhexanoic acid ($C_6$), (R)-(–)-3-hydroxyoctanoic acid ($C_8$), and (R)-(–)-3-hydroxydecanoic acid ($C_{10}$). (R)-(–)-3-hydroxyoctanoic acid is the major monomer among the above, being 86 mol %. The fraction of (R)-(–)-3-hydroxyhexanoic acid is 10 mol % and that of (R)-(–)-3-hydroxydecanoic acid being 4 mol %. Particularly in this case, the synthesized polymer is conveniently called as poly-(R)-(–)-3-hydroxyhexanoate-co-(R)-(–)-3-hydroxyoctan oate, since most of the monomers contained in the synthesized PHA are (R)-(–)-3-hydroxyoctanoic acid and (R)-(–)-3-hydroxyhexanoic acid.

If nonanoic acid is used as a carbon source, the synthesized PHA consists of six kinds of monomers as in the case of using heptanoic acid. (R)-(–)-3-hydroxynonanoic acid is the major monomer, being 58 mol %. The fractions of (R)-(–)-3-hydroxyheptanoic acid, (R)-(–)-3-hydroxyoctanoic acid, (R)-(–)-3-hydroxydecanoic acid and that of (R)-(–)-3-hydroxyhexanoic acid are 31, 6, 3 and 1 mol %, respectively. And little (R)-(–)-3-hydroxyundecanoic acid also exists.

If decanoic acid is used as a carbon source, the synthesized PHA consists of five kinds of monomers, which are $C_6$, $C_8$, $C_9$, $C_{10}$ and $C_{11}$. (R)-(–)-3-hydroxyoctanoic acid is the major monomer, being 63 mol %. The fractions of (R)-(–)-3-hydroxyhexanoic acid, (R)-(–)-3-hydroxydecanoic acid (R)-(–)-3-hydroxyundecanoic acid and that of (R)-(–)-3-hydroxynonanoic acid are 20, 11, 3 and 1 mol %, respectively.

Therefore, it is preferable that (R)-(–)-3-hydroxyhexanoic acid is produced from hexanoic acid; (R)-(–)-3-hydroxyheptanoic acid from heptanoic acid; (R)-(–)-3-hydroxyoctanoic acid from octanoic acid; (R)-(–)-3-hydroxynonanoic acid from nonanoic acid; and (R)-(–)-3-hydroxydecanoic acid and (R)-(–)-3-hydroxyundecanoic acid from decanoic acid.

In this example, sodium octanoate or nonanoic acid was used as a carbon source to produce medium chain length PHAs, and subsequently their monomers by auto-degradation. *Pseudomonas oleovorans* ATCC 29347 was cultured in a chemically defined medium containing only sodium octanoate or nonanoic acid as a carbon source by the method described previously (Lee, *Biotechnol. Bioprocess Eng.*, 1: 51–53, 1996). Cells accumulated copolymers to the levels of 5% to 40% of cell dry weight. When sodium octanoate was used as a carbon source, cells accumulated PHA copolymers to 20% of cell dry weight. When nonanoic acid was used as a carbon source, cells accumulated PHA copolymers up to 18% of cell dry weight. Cells collected by centrifugation were dispersed into the water, which was adjusted to pH 7.0, at a concentration of 75 g cell dry weight/L, and auto-degradation reaction was carried out at 30° C. for 4 days (Table 7 and Table 8).

TABLE 7

Production of medium chain length (R)—(—)-3-hydroxycarboxylic acids by auto-degradation of PHAs produced in *Pseudomonas oleovorans* ATCC 29347 by culturing on sodium octanate as a carbon source (initial pH: 7.0, reaction temperature: 30° C., reaction time: 4 days).

| Monomer | Mole fraction in polymer (%) | Produced amount (g/L) | Yield (%) |
|---|---|---|---|
| (R)—(—)-3-hydroxyhexanoic acid | 10 | 0.13 | 9.2 |
| (R)—(—)-3-hydroxyoctanoic acid | 86 | 1.42 | 9.7 |
| (R)—(—)-3-hydroxydecanoic acid | 4 | — | 0 |

TABLE 8

Production of medium chain length (R)—(—)-3-hydroxycarboxylic acids by auto-degradation of PHAs produced in *Pseudomonas oleovorans* ATCC 29347 by culturing on nonanoic acid as a carbon source (initial pH: 7.0, reaction temperature: 30° C., reaction time: 4 days).

| Monomer | Mole fraction in polymer (%) | Produced amount (g/L) | Yield (%) |
|---|---|---|---|
| (R)—(—)-3-hydroxyhexanoic acid | 1 | — | 0 |
| (R)—(—)-3-hydroxyheptanoic acid | 31 | 0.35 | 8.3 |
| (R)—(—)-3-hydroxyoctanoic acid | 6 | — | 0 |
| (R)—(—)-3-hydroxynonanoic acid | 58 | 0.89 | 9.47 |
| (R)—(—)-3-hydroxydecanoic acid | 3 | — | 0 |

As shown in Table 7 and Table 8, the yields of the major monomers, which were produced by auto-degradation, were 8–10%.

Until now, there has been no report on the method for producing medium chain length (R)-(−)-3-hydroxycarboxylic acids. Medium chain length (R)-(−)-3-hydroxycarboxylic acid could be produced by the method described in the present invention even though the efficiency was somewhat lower than (R)-(−)-3-hydroxybutyric acid. Furthermore, other medium chain length (R)-(−)-3-hydroxycarboxylic acid monomers can also be produced by changing a carbon source during PHA accumulation.

EXAMPLE 12

Preparation of Optically Active Medium Chain Length Hydroxycarboxylic Acids by Auto-degradation of PHAs, Which are Synthesized and Accumulated in *Pseudomonas aeruginosa*

It was reported that when *Pseudomonas aeruginosa* AO232 is cultured using acetic acid as a carbon source, PHAs consisting of $C_6$, $C_8$, $C_{10}$ and $C_{12}$ compound ((R)-(−)-3-hydroxyhexanoic acid, (R)-(−)-3-hydroxyoctanoic acid, (R)-(−)-3-hydroxydecanoic acid and (R)-(−)-3-hydroxydodecanoic acid) are synthesized and accumulated; and using propionic acid as a carbon source, PHAs consisting of seven different monomers of $C_6$–$C_{12}$ compound ((R)-(−)-3-hydroxyhexanoic acid, (R)-(−)-3-hydroxyheptanoic acid, (R)-(−)-3-hydroxyoctanoic acid, (R)-(−)-3-hydroxynonanoic acid, (R)-(−)-3-hydroxydecanoic acid, (R)-(−)-3-hydroxyundecanoic acid and (R)-(−)-3-hydroxydodecanoic acid) are synthesized and accumulated (Saito and Doi, *Int. J. Biol. Macromol.*, 15: 287, 1993; Lee and Chang, *Adv. Biochem. Eng.*, 52: 27–58, 1995).

In addition, it was reported that *Pseudomonas putida* transformed with a plasmid containing the PHA synthase of *Pseudomonas aeruginosa* PAO1 could synthesize PHAs consisting of monomers, $C_6$, $C_8$, $C_{10}$ and $C_{12}$ compound ((R)-(−)-3-hydroxyhexanoic acid, (R)-(−)-3-hydroxyoctanoic acid, (R)-(−)-3-hydroxydecanoic acid and (R)-(−)-3-hydroxydodecanoic acid) when cultivated using gluconate as a carbon source (Timm and Steinbuchel, *Eur. J. Biochem.*, 209: 15–30, 1992).

Therefore, it was reasoned that various medium chain length (R)-(−)-3-hydroxycarboxylic acids can be prepared by auto-degradation using *Pseudomonas aeruginosa*, and particularly, (R)-(−)-3-hydroxydodecanoic acid can be prepared.

In this example, *Pseudomonas aeruginosa* PAO1 DSM 1707 was cultured in a chemically defined medium containing gluconate as a carbon source as reported previously (Timm and Steinbuchel, *Eur. J. Biochem.*, 209: 15–30, 1992), and then the cultured cells were dispersed to give the PHA concentration of 15 g/L in water, which was adjusted to pH 7.0. Auto-degradation was carried out at 30° C. for 4 days to prepare medium chain length hydroxycarboxylic acids. (Table 9).

TABLE 9

Production of medium chain length (R)—(—)-3-hydroxycarboxylic acids by auto-degradation of PHAs produced in *Pseudomonas aeruginosa* PA01 DSM 1707 by culturing on gluconate as a carbon source (initial pH: 7.0, reaction temperature: 30° C., reaction time: 4 days).

| Monomer | Mole fraction in polymer (%) | Produced amount (g/L) | Yield (%) |
|---|---|---|---|
| (R)—(—)-3-hydroxyhexanoic acid | 3 | — | 0 |
| (R)—(—)-3-hydroxyoctanoic acid | 24 | 0.34 | 9.6 |
| (R)—(—)-3-hydroxydecanoic acid | 67 | 1.02 | 8.8 |
| (R)—(—)-3-hydroxydodecanoic acid | 6 | 0.08 | 6.7 |

As shown in Table 9, (R)-(−)-3-hydroxyoctanoic acid, (R)-(−)-3-hydroxydecanic acid and (R)-(−)-3-hydroxydodecanoic acid could be produced with a yield of 6 to 10%, and these three compounds could be separated by LC or HPLC.

Therefore, medium chain length (R)-(−)-3-hydroxycarboxylic acids could be prepared by auto-degradation of PHAs accumulated in *Pseudomonas aeruginosa*. And particularly, the method of preparing (R)-(−)-3-hydroxydecanoic acid and (R)-(−)-3-hydroxydodecanoic acid was provided by this example.

EXAMPLE 13

Preparation of Optically Active Medium Chain Length Hydroxyalkanoic Acids and (R)-(−)-3-hydroxy-5-phenylvaleric Acid by Auto-degradation of PHA, Which is Synthesized and Accumulated in *Pseudomonas oleovorans* by Using 5-phenylvaleric Acid as Cosubstrate with Nonanoic Acid In this example, it was examined to see if PHAs containing unusual monomer constituents could be auto-degraded to give the corresponding optically active monomers.

As previously reported (Fritzsche et al., *Makromol. Chem.*, 191: 1957, 1990; Kim et al., Macromol., 24: 5256, 1991), *Pseudomonas oleovorans* can produce PHAs which contain optically active 3-hydroxy-5-phenylvaleric acid monomer unit when they are grown in the presence of 5-phenylvaleric acid. In this example, *Pseudomonas oleovorans* ATCC 29347 was grown with mixed substrates (10 mM total with 2:1 molar ratio of 5-phenylvaleric acid to nonanoic acid). The final PHA content was 22% and the fraction of 3-hydroxy-5-phenylvaleric acid monomer unit in PHA was 35 mol %. The PHA containing cells were harvested and resuspended in water (pH was initially adjusted to 7.0) at 20 g/L of initial PHA concentration, and then incubated at 37° C. for 4 days. The resulted amounts of produced (R)-(−)-3-hydroxyheptanoic acid, (R)-(−)-3-hydroxynonanoic acid and (R)-(−)-3-hydroxy-5-phenylvaleric acid were 0.18, 0.65 and 0.62 g/L, and the yields were 7.0%, 8.1% and 8.0%, respectively.

This example demonstrated that (R)-(−)-3-hydroxy-5-phenylvaleric acid monomer unit, even though the monomer unit is unusual for microbial PHA, can be produced by auto-degradation of PHA containing this monomer. From this result, unusual PHAs accumulated in microorganisms can be degraded to obtain the corresponding optically active monomers by using auto-degradation method described in the present invention.

As described in the above examples, various (R)-(−)-hydroxycarboxylic acids could be efficiently produced by auto-degradation of PHAs accumulated in various microorganisms. The monomer yields were high, which makes this process economically attractive. For the case of (R)-(−)-3-hydroxybutyric acid, the efficiency of monomer production by the methods described in the present invention can be compared with that previously reported by Akira and Tatsuhiko (JP9-234091, 1997). As summarized below (Table 10), the (R)-(−)-3-hydroxybutyric acid yield obtained by the method described in the present invention was up to 50 times higher than that obtained by the method described in JP9-234091. Therefore, the method described in the present invention provides much more efficient and economical way of producing (R)-(−)-3-hydroxybutyric acid. Furthermore, the method described in the present invention is not limited to the production of (R)-(−)-3-hydroxybutyric acid, and can be used to produce a variety of (R)-(−)-hydroxycarboxylic acids as demonstrated in the above examples. It is obvious that any wild type microorganisms accumulating PHAs and possessing intracellular depolymerase activity can be used for the production of various (R)-(−)-hydroxycarboxylic acids. Furthermore, it is obvious that mutant strains of the above said microorganisms can also be used for the production of (R)-(−)-hydroxycarboxylic acids as long as they possess intracellular PHA depolymerase activity.

TABLE 10

Summary of the yields of (R)—(—)-3-hydroxybutyric acid produced by auto-degradation

| | Microorganisms | Yield of (R)—(—)-3-hydroxybutyric acid (g/g PHB) |
|---|---|---|
| Example 1 | Alcaligenes latus DSM 1123 | 0.94 |
| Example 2 | Alcaligenes latus DSM 1123 | 1.02 |
| Example 4 | Ralstonia eutropha NCIMB 11599 | 0.27 |
| Example 6 | Corynebacterium sp. SS-15 | 1.01 |
| Example 7 | Bacillus sp. SS-19 | 0.69 |
| Example 8 | Methylosinus trichosporium KCTC 2591 | 0.11 |
| Example 9 | Rhodospirillum rubrum KCTC 1372 | 0.13 |
| Example 10 | Ralstonia eutropha H16 ATCC 17699 | 0.28 |
| Example 13 | recombinant Ralstonia eutropha | 0.29 |
| Comparison Example 1 | Pseudomonas sp. FM13 | 0.05–0.08 |
| Comparison Example 2 | Ralstonia eutropha ATCC 12567 | 0.02–0.03 |

*Comparison Example 1 and Comparison Example 2 are the calculated results reported in the Japanese patent JP9-234091 with the assumption that the PHB contents were ca. 50–80% related to cell dry weight.

EXAMPLE 14

Preparation of (R)-(−)-3-hydroxybutyric Acid by Auto-degradation of PHB, Which is Synthesized and Accumulated in Recombinant Ralstonia eutropha In the above examples (Example 1 to Example 13), it was provided how to prepare (R)-(−)-hydroxycarboxylic acids by auto-degradation of PHA polymers, which were synthesized and accumulated in non-recombinant microorganisms. Recently, there have been several reports on the cloning of the PHA biosynthesis genes from several microorganisms and on enhancing polymer production by recombinant microorganisms containing the amplified PHA biosynthetic enzyme activities (Lee, Biotechnol. Bioeng., 49: 1–14, 1996; Lee, Trends Biotechnol., 14: 431–438, 1996; Steinbuchel et al., FEMS Microbiol. Rev., 103: 217–230, 1992 and references cited therein).

In this example, a recombinant microorganism, which can synthesize and accumulate PHA, was used to prepare (R)-(−)-hydroxycarboxylic acid by auto-degradation.

Ralstonia eutropha NCIMB 11599 which was transformed with the broad-host-range plasmid pVK101 (Knauf and Nester, Plasmid, 8: 45, 1982) containing the PHA biosynthesis genes of Ralstonia eutropha ATCC 17699 (Schubert et al., J. Bacteriol., 170: 5837–5847, 1988; Choi and Lee, Hwahak Konghak, 35: 684–689, 1997), was cultured by the method reported previously (Kim et al., Biotechnol. Bioeng., 43: 892–898, 1994). Cells accumulated PHB to 66% of cell dry weight. Cells collected by centrifugation were dispersed in water, which was adjusted to pH 4.0 or 7.0, to give the initial PHB concentration of 30 g/L and kept at 30° C. for 35 hours.

When the initial pH was 4.0, 5 g/L of (R)-(−)-3-hydroxybutyric acid and 0.3 g/L of the dimer were obtained, while 8.7 g/L of (R)-(−)-3-hydroxybutyric acid and 0.6 g/L of the dimer were obtained when pH was 7.0. The yields were 14.7% and 26.8%, respectively. Therefore, it was proved that recombinant microorganisms, as long as they possess intracellular depolymerase activity, can also be used to prepare (R)-(−)-3-hydroxybutyric acid by auto-degradation of PHA accumulated in the recombinant microorganism.

EXAMPLE 15

Auto-degradation of PHB Synthesized and Accumulated in Recombinant Escherichia coli Harboring Heterologous PHA Biosynthesis Genes The host microorganism, Ralstonia eutropha (formerly Alcaligenes eutrophus) NCIMB 11599, used in Example 14 has PHA synthesis activity naturally, even before the transformation with the PHA biosynthesis genes. In this example, two Escherichia coli strains, which do not have PHA synthesis activity naturally (and thus cannot accumulate PHA intracellularly), were used as host microorganism, and were transformed with a plasmid containing the Raistonia eutropha H16 ATCC 17699 or the Alcaligenes latus DSM 1123 PHA biosynthesis genes.

Recombinant E. coli B ATCC 11303 and E. coli XL1-Blue (Stratagene Cloning Systems, La Jolla, Calif. 92037) were used in this example, which were transformed with high-copy-number plasmid pSYL105 containing *Alcaligenes eutrophus* PHA biosynthesis genes (Lee et al., *Biotechnol. Bioeng.*, 44: 1337–1347, 1994) or pJC4 (KCTC 0481BP) containing the *Alcaligenes latus* PHA biosynthesis genes (Choi et al., *Appl. Environ. Microbiol.*, in press (December, 1998); Lee et al., Korean Patent application No. 98-1423, 1998). These recombinant *E. coli* strains were cultured in LB medium (pH 7.0) containing 20 g/L of glucose as a carbon source by the method reported previously (Lee et al., *Biotechnol. Bioeng.*, 44: 1337–1347, 1994) in flasks. Cells accumulating PHB to 75%–80% of cell dry weight were collected by centrifugation. Auto-degradation was carried out at various initial pH (pH 4, 7 and 10) and various reaction temperatures (20, 30, 37 and 45° C.). Under any condition employing various recombinant *E. coli* strains, (R)-(−)-3-hydroxybutyric acid production was not detected even after 4 days.

As shown in the above examples (Example 14 and 15), in case that recombinant microorganism has natural PHA synthesis activity, (R)-(−)-hydroxycarboxylic acid can be produced by auto-degradation from the microorganism because the microorganism also has intracellular PHA depolymerase. But in case that recombinant microorganism which does not have PHA synthesis activity naturally like *E. coli*, (R)-(−)-hydroxycarboxylic acid can not be produced by auto-degradation from the microorganism because the microorganism does not have intracellular PHA depolymerase. However, if a recombinant microorganism, which does not have the natural PHA synthesis activity, is transformed with a plasmid containing a cloned intracellular PHA depolymerase gene as well as PHA synthesis genes, the monomers can be produced by the transformed microorganism by auto-degradation method. Therefore, recombinant microorganisms can be used to produce (R)-(−)-hydroxycarboxylic acid monomers by auto-degradation of PHA accumulated therein, as long as they naturally have or acquired by recombinant DNA techniques the intracellular PHA depolymerase activity.

EXAMPLE 16

Separation of Optically Pure Hydroxycarboxylic Acid Monomers Using HPLC

Figure 6:
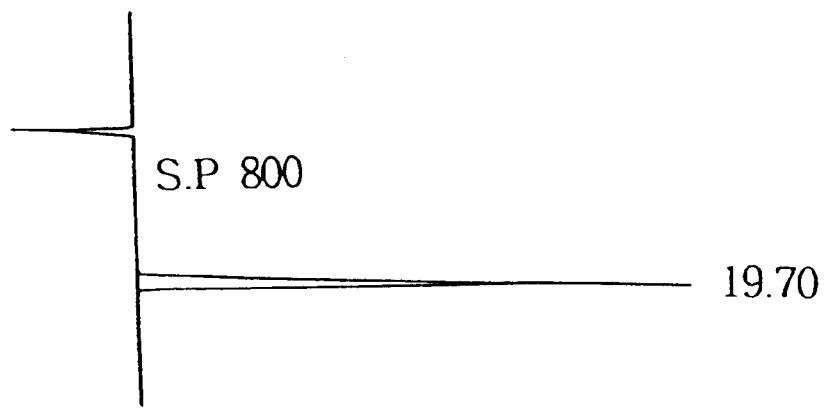
FIG. 6 shows the standard HPLC peak profile of commercial 4-hydroxybutyric acid (Sigma chemical Co., USA).
Figure 8:
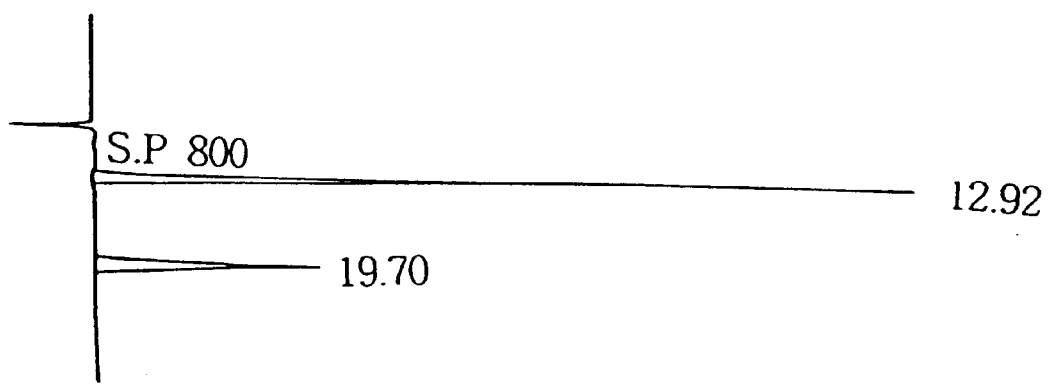
FIG. 8 shows the HPLC peak profile of (R)-(−)-3-hydroxybutyric acid and 4-hydroxybutyric acid obtained by auto-degradation of poly-(R)-(−)-3-hydroxybutyrate-co-4-hydroxybutyrate copolymer accumulated in *Alcaligenes latus*.

The mixture of hydroxycarboxylic acid monomers, which were produced by auto-degradation of PHAs copolymers, could be separated easily by conventional well known methods such as ion exchange, electrodialysis, extraction, distillation, liquid chromatography (LC) and high performance liquid chromatography (HPLC). For a preferable example, (R)-(−)-3-hydroxybutyric acid and 4-hydroxybutyric acid prepared in Example 3 were separated using HPLC (FIG. 5, FIG. 6 and FIG. 8).

In detail, hydroxycarboxylic acid monomers were separated and purified by HPLC (Hitachi Co., Japan), which was equipped with Hitachi L-6000 pump, L-3300 RI detector, and organic acid-separating column such as Aminex® HPX-87H column (Bio-Rad lab. Co., USA) or ORH-801 column (Rainin Co., USA). 0.01N $H_2SO_4$ solution was used as the mobile phase. As can be seen in FIGS. 5, 6 and 8, two monomers were efficiently separated. Aminex® HPX-87H column is one of the commonly used ion-exchange columns in separation and analysis of sugars and organic acids. Therefore, LC or HPLC equipped with ion-exchange column can efficiently separate hydroxycarboxylic acid monomers. Moreover, the use of ion-exchange columns has strong advantage of easy scaling-up. For the separation of longer chain length monomers such as medium chain length hydroxycarboxylic acids, the use of hydrophobic interaction columns is also possible.

EXAMPLE 17

Purification of (R)-(−)-hydroxycarboxylic Acids

The monomers, which were prepared from homopolymer such as poly-(R)-(−)-3-hydroxybutyrate, and (R)-(−)-hydroxycarboxylic acid monomers, which were purely separated by the method shown in Example 16 after auto-degradation of copolymer, can be further purified by conventional chemical methods or by the methods described below to make final products for appropriate use.

In this example, two preferred processes were examined for purification of (R)-(−)-3-hydroxybutyric acid prepared in Example 1 and Example 2.

The one is a modified method of Seebach et al. (Seebach et al., *Org. Synth.*, 71: 39–47, 1992): 1 mL of 0.1N sodium hydroxide was added to 10 mL of (R)-(−)-3-hydroxybutyric acid-sulfuric acid solution (200 g/L (R)-(−)-3-hydroxybutyric acid) to neutralize, and the water was removed using rotary evaporator. Then, 20 mL of ether was added to dissolve the mixture and anhydrous magnesium sulfate was added to desiccate. Finally the mixture was filtered. The added ether was also evaporated to concentrate using rotary evaporator and distilled under reduced pressure at 100° C. using Kugelrohr (Aldrich Co., USA). As a result, about 1.58 g of (R)-(−)-3-hydroxybutyric acid (about 79% of yield) was obtained with a purity higher than 90%.

In the above method, much energy was needed in the purifying process such as distillation under reduced pressure, which would increase the production cost. Therefore, another purifying process was developed as shown below.

Firstly, 10 mL of (R)-(−)-3-hydroxybutyric acid solution (200 g/L (R)-(−)-3-hydroxybutyric acid) was adjusted to the pH of 11 by adding sodium hydroxide. Then, impurities were removed by solvent extraction with 10 mL of chloroform or ether (impurities were extracted into the organic phase). The aqueous phase containing product was dried in drying oven at 95° C. The resulting dry matter was dissolved in ethanol and dried again. Finally, about 1.97 g of (R)-(−)-3-hydroxybutyric acid-sodium salt was obtained as a powder form (about 82% of yield) with purity higher than 90%. In this process, another strong alkali such as potassium hydroxide in addition to sodium hydroxide can be used to adjust pH to alkaline range, which does not affect the process except the change of the sort of final salt form.

In addition, chloroform and ether used in this example as extraction solvent to remove impurities can be replaced by any other organic solvents, which are immiscible with water, without much affecting the process.

The method of Seebach et al. (Seebach et al., *Org. Synth.*, 71: 39–47, 1992) is difficult to employ in practice because the process requires high operating costs and complex equipments. Therefore, the latter process, which is developed in the present invention, is more applicable for practical use and (R)-(−)-3-hydroxybutyric acid can be purified and powder-made efficiently by the process.

Only (R)-(−)-3-hydroxybutyric acid was purified in this example but this purifying process can be used for the purification of any other (R)-(−)-hydroxycarboxylic acid monomers with high purity.

EXAMPLE 18

Figure 9:
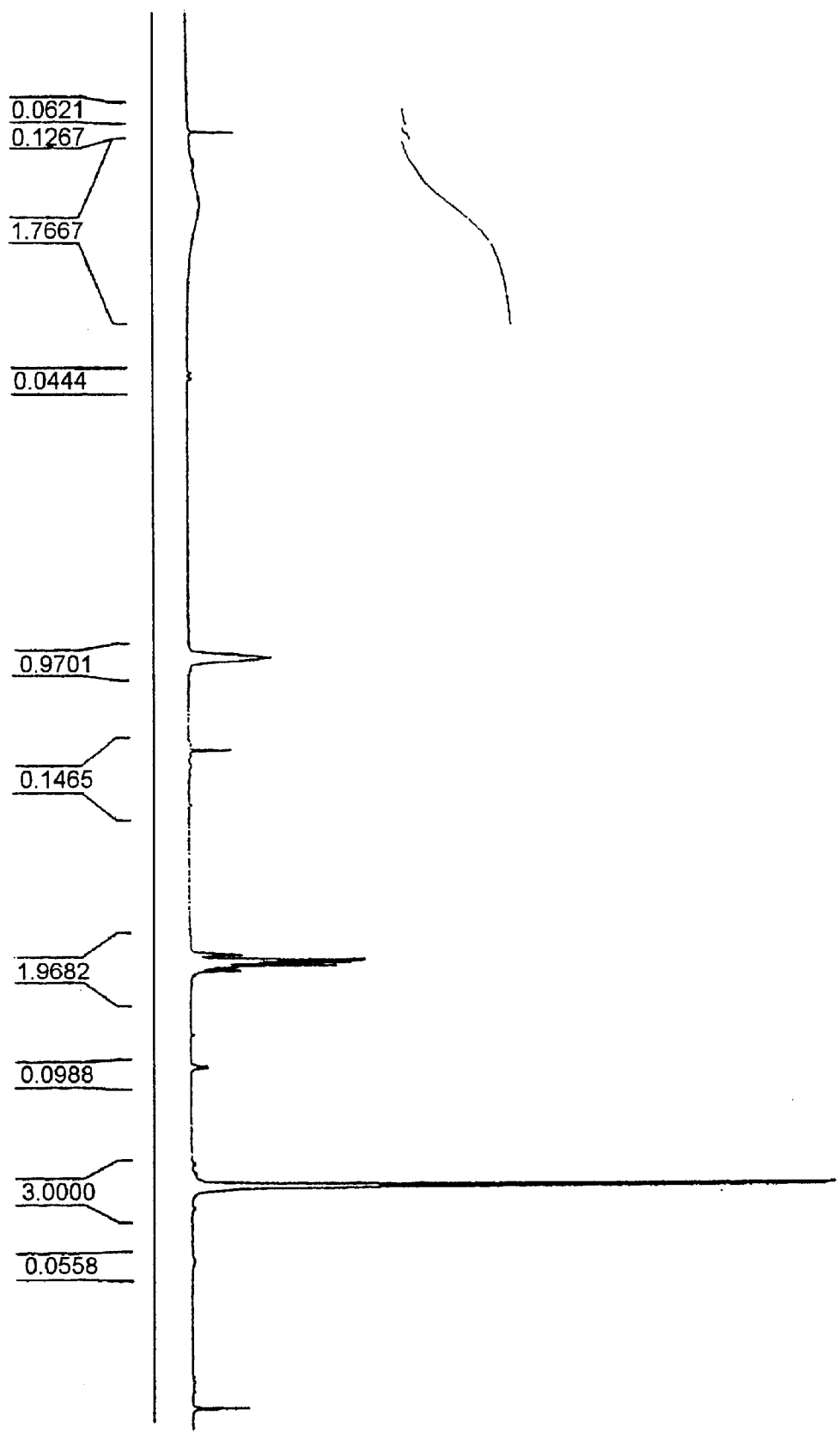
FIG. 9 shows the $H^1$ NMR peak profile of purified (R)-(−)-3-hydroxybutyric acid by auto-degradation of PHB accumulated in *Alcaligenes latus*.

Identification of Purified (R)-(−)-3-hydroxycarboxylic Acids and Examination of Optical Purity The purified product was dissolved in $CDCl_3$ and analyzed by proton NMR (Bruker, Germany) to prove that the purified product was (R)-(−)-3-hydroxybutyric acid. As shown in FIG. 9, it was proved that the purified product was (R)-(−)-3-hydroxybutyric acid. PHAs, which are accumulated in a microorganism, are made up of only optically active monomer units with (R)-(−)-configuration due to the optical specificity of biosynthesis enzyme, if the monomer units have optical isomer (no isomers for 3-hydroxypropionic acid, 4-hydroxybutyric acid, 5-hydroxyvaleric acid and 3-hydroxy-2-butenoic acid). Therefore, all the produced monomer units are theoretically optically pure. To prove this, the purified powder was dissolved in distilled water and optical rotation was measured by using polarimeter (Perkin-Elmer Co., USA). The optical rotation was −24.7°, which was in good agreement with the value reported by Seebach et al. (Seebach et al., *Org. Synth.*, 71: 39–47, 1992), thus it was proved that the purified (R)-(−)-3-hydroxybutyric acid was optically pure.

EFFECT OF THE INVENTION

As described clearly in the above, various optically active hydroxycarboxylic acids can be prepared by auto-degradation of various PHAs, which are synthesized and accumulated in various microorganisms, and the produced monomers can be separated easily if they exist as mixture of two or more monomers. In addition, purely-separated (R)-(−)-hydroxycarboxylic acid can be further purified by organic solvent extraction, which remove impurities, and pulverized by drying. The method for the production of various (R)-(−)-hydroxycarboxylic acids developed in the present invention is economical because optically active (R)-(−)-hydroxycarboxylic acids can be efficiently produced with high yield and purity by simple process. Also, this process is environmentally friendly because organic solvents, which are required in large amounts in conventional methods, are used in only minimal amounts in the present invention.

What is claimed is:

1. A method for producing various optically active (R)-(−)-hydroxycarboxylic acids comprising the steps of:

a) synthesizing and accumulating polyhydroxyalkanoates (PHA) in a cell of a microorganism by culturing the microorganism having an intracellular polyhydroxyalkanoate depolymerase activity in a medium;

b) collecting the cultured microorganism from the medium;

c) contacting the collected cultured microorganism with a degradation solution free of carbon source wherein PHA accumulated in the cell of the microorganism is subjected to microbial enzyme degradation into the corresponding monomers and the produced monomers are secreted into solution; and d) separating the produced monomer from the solution.

2. The method of claim 1 wherein said microorganism is selected from the group consisting of microorganisms of the genus Achromobacter, microorganisms of the genus Acidovorax, microorganisms of the genus Acinetobacter, Actinobacillus sp., Actinomyces sp., *Aeromonas caviae*, microorganisms of the genus Alcaligenes, *Alteromonas macleodii*, microorganisms of the genus Amoebobacter, Aphanocapsa sp., Aphanothece sp., *Aquaspirillum autotrophicum, Azorhizobium caulinodans*, microorganisms of the genus Azospirillum, microorganisms of the genus Azotobacter, microorganisms of the genus Bacillus, microorganisms of the genus Beggiatoa, microorganisms of the genus Beijerinckia, microorganisms of the genus Beneckea, *Bordetella pertussis, Bradyrhizobium japonicum, Caryophanon latum*, microorganisms of the genus Caulobacter, *Chloroflexus aurantiacus*, microorganisms of the genus Chlorogloea, microorganisms of the genus Chromatium, microorganisms of the genus Chromobacterium, microorganisms of the genus Clostridium, microorganisms of the genus Comamonas, microorganisms of the genus Corynebacterium, microorganisms of the genus Derxia, *Desulfococcus multivorans*, microorganisms of the genus Desulfonema, *Desulfosarcina variabilis*, microorganisms of the genus Desulfovibrio, microorganisms of the genus Ectothiorhodospira, Ferrobacillus ferrooxidans, Flavobacterium sp., *Haemophilus influenzae*, microorganisms of the genus Halobacterium, *Haloferax mediterranei, Hydroclathratus clathratus, Hydrogenomonas facilis*, microorganisms of the genus Hydrogenophaga, microorganisms of the genus Hyphomicrobium, *Ilyobacter delafieldii, Labrys monachus*, microorganisms of the genus Lactobacillus, microorganisms of the genus Lactococcus, *Lamprocystis roseopersicina, Lampropedia hyalina*, Legionella sp., *Leptothrix discophorus*, microorganisms of the genus Methylobacterium, *Methylococcus thermophilus, Methylocystis parvus, Methylomonas methanica*, microorganisms of the genus Methylosinus, *Methylovibrio soehngenii*, microorganisms of the genus Micrococcus, microorganisms of the genus Microcoleus, microorganisms of the genus Microcystis, microorganisms of the genus Moraxella, microorganisms of the genus Mycobacterium, *Mycoplana rubra*, microorganisms of the genus Nitrobacter, microorganisms of the genus Nitrococcus, microorganisms of the genus Nocardia, *Oscillatoria limosa, Paracoccus dentrificans, Pediococcus halophilus, Penicillium cyclopium*, microorganisms of the genus Photobacterium, *Physarum polycephalum, Protomonas extorquens*, microorganisms of the genus Pseudomonas, microorganisms of the genus Ralstonia, microorganisms of the genus Rhizobium, microorganisms of the genus Rhodobacillus, microorganisms of the genus Rhodobacter, microorganisms of the genus Rhodococcus, microorganisms of the genus Rhodocyclus, *Rhodomicrobium vannielii*, microorganisms of the genus Rhodopseudomonas, microorganisms of the genus Rhodospirillum, *Sphaerotilus natans, Sphingomonas paucimobilis*; microorganisms of the genus Spirillum, microorganisms of the genus Spirulina, microorganisms of the genus Staphylococcus, microorganisms of the genus Stella, *Streptococcus thermophilus,* microorganisms of the genus Streptomyces, microorganisms of the genus Synechococcus, *Syntrophomonas wolfei,* microorganisms of the genus Thiobacillus, microorganisms of the genus Thiocapsa, *Thiocystis violacea,* microorganisms of the genus Thiodictyon, *Thiosphaera pantotropha, Trichodesmimum thiebautii, Vibrio parahaemolyticus, Xanthobacter autotrophicus, Xanthomonas maltophilia* and microorganisms of the genus Zoogloea.

3. The method of claim 1 wherein said monomer is one or more selected from the group consisting of 3-hydroxypropionic acid, (R)-(–)-3-hydroxyvaleric acid, (R)-(–)-3-hydroxyhexanoic acid, (R)-(–)-3-hydroxyheptanoic acid, (R)-(–)-3-hydroxyoctanoic acid, (R)-(–)-3-hydroxynonanoic acid, (R)-(–)-3-hydroxydecanoic acid, (R)-(–)-3-hydroxyundecanoic acid, (R)-(–)-3-hydroxydodecanoic acid, (R)-(–)-3-hydroxytetradecanoic acid, (R)-(–)-3-hydroxyhexadecanoic acid, 4-hydroxybutyric acid, (R)-(–)-4-hydroxyvaleric acid, (R)-(–)-4-hydroxyhexanoic acid, (R)-(–)-4-hydroxyheptanoic acid, (R)-(–)-4-hydroxyoctanoic acid, (R)-(–)-4-hydroxydecanoic acid, 5-hydroxyvaleric acid, (R)-(–)-5-hydroxyhexanoic acid, (R)-(–)-6-hydroxydodecanoic acid, (R)-(–)-3-hydroxy-4-pentenoic acid, (R)-(–)-3-hydroxy-4-trans-hexenoic acid, (R)-(–)-3-hydroxy-4-cis-hexenoic acid, (R)-(–)-3-hydroxy-5-hexenoic acid, (R)-(–)-3-hydroxy-6-trans-octenoic acid, (R)-(–)-3-hydroxy-6-cis-octenoic acid, (R)-(–)-3-hydroxy-7-octenoic acid, (R)-(–)-3-hydroxy-8-nonenoic acid, (R)-(–)-3-hydroxy-9-decenoic acid, (R)-(–)-3-hydroxy-5-cis-dodecenoic acid, (R)-(–)-3-hydroxy-6-cis-dodecenoic acid, (R)-(–)-3-hydroxy-5-cis-tetradecenoic acid, (R)-(–)-3-hydroxy-7-cis-tetradecenoic acid, (R)-(–)-3-hydroxy-5,8-cis-cis-tetradecenoic acid, (R)-(–)-3-hydroxy-4-methylvaleric acid, (R)-(–)-3-hydroxy-4-methylhexanoic acid, (R)-(–)-3-hydroxy-5-methylhexanoic acid, (R)-(–)-3-hydroxy-6-methylheptanoic acid, (R)-(–)-3-hydroxy-4-methyloctanoic acid, (R)-(–)-3-hydroxy-5-methyloctanoic acid, (R)-(–)-3-hydroxy-6-methyloctanoic acid, (R)-(–)-3-hydroxy-7-methyloctanoic acid, (R)-(–)-3-hydroxy-6-methylnonanoic acid, (R)-(–)-3-hydroxy-7-methylnonanoic acid, (R)-(–)-3-hydroxy-8-methylnonanoic acid, (R)-(–)-3-hydroxy-7-methyldecanoic acid, (R)-(–)-3-hydroxy-9-methyldecanoic acid, (R)-(–)-3-hydroxy-7-methyl-6-octenoic acid, malic acid, (R)-(–)-3-hydroxysuccinic acid-methyl ester, (R)-(–)-3-hydroxyadipinic acid-methyl ester, (R)-(–)-3-hydroxysuberic acid-methyl ester, (R)-(–)-3-hydroxyazelaic acid-methyl ester, (R)-(–)-3-hydroxysebacic acid-methyl ester, (R)-(–)-3-hydroxysuberic acid-ethyl ester, (R)-(–)-3-hydroxysebacic acid-ethyl ester, (R)-(–)-3-hydroxypimelic acid-propyl ester, (R)-(–)-3-hydroxysebacic acid-benzyl ester, (R)-(–)-3-hydroxy-8-acetoxyoctanoic acid, (R)-(–)-3-hydroxy-9-acetoxynonanoic acid, phenoxy-(R)-(–)-3-hydroxybutyric acid, phenoxy-(R)-(–)-3-hydroxyvaleric acid, phenoxy-(R)-(–)-3-hydroxyheptanoic acid, phenoxy-(R)-(–)-3-hydroxyoctanoic acid, para-cyanophenoxy-(R)-(–)-3-hydroxybutyric acid, para-cyanophenoxy-(R)-(–)-3-hydroxyvaleric acid, para-cyanophenoxy-(R)-(–)-3-hydroxyhexanoic acid, para-nitrophenoxy-(R)-(–)-3-hydroxyhexanoic acid, (R)-(–)-3-hydroxy-5-phenylvaleric acid, (R)-(–)-3-hydroxy-5-cyclohexylbutyric acid, (R)-(–)-3,12-dihydroxydodecanoic acid, (R)-(–)-3,8-dihydroxy-5-cis-tetradecenoic acid, (R)-(–)-3-hydroxy-4,5-epoxydecanoic acid, (R)-(–)-3-hydroxy-6,7-epoxydodecanoic acid, (R)-(–)-3-hydroxy-8,9-epoxy-5,6-cis-tetradecanoic acid, 7-cyano-(R)-(–)-3-hydroxyheptanoic acid, 9-cyano-(R)-(–)-3-hydroxynonanoic acid, (R)-(–)-3-hydroxy-7-fluoroheptanoic acid, (R)-(–)-3-hydroxy-9-fluorononanoic acid, (R)-(–)-3-hydroxy-6-chlorohexanoic acid, (R)-(–)-3-hydroxy-8-chlorooctanoic acid, (R)-(–)-3-hydroxy-6-bromohexanoic acid, (R)-(–)-3-hydroxy-8-bromooctanoic acid, (R)-(–)-3-hydroxy-11-bromoundecanoic acid, 3-hydroxy-2-butenoic acid, (R)-(–)-6-hydroxy-3-dodecenoic acid, (R)-(–)-3-hydroxy-2-methylbutyric acid, (R)-(–)-3-hydroxy-2-methylvaleric acid and (R)-(–)-3-hydroxy-2,6-dmethyl-5-heptenoic acid.

4. The method of claim 1 wherein said microorganism is selected from the group consisting of microorganisms of *Alcaligenes latus*, Corynebacterium sp., Bacillus sp., *Methylosinus trichosporium, Rhodospirillum rubrum, Ralstonia eutropha, Pseudomonas aeruginosa* and *Pseudomonas oleovorans.*

5. The method of claim 1 wherein said microorganism is *Pseudomonas aeruginosa* or *Pseudomonas oleovorans,* and said monomer is one or more selected from the (R)-(–)-3-hydroxycarboxylic acids of which carbon numbers are in the range of 6 to 14.

6. The method of claim 1 including adjusting the pH of said solution of step c) to a range of 2–12, and performing step c) at a temperature in the range of 4–60° C., for a time of greater than 0.5 h.

7. The method of claim 1, wherein the step d) is performed with liquid chromatography (LC) and high performance liquid chromatography (HPLC).

8. The method of claim 1, further comprising the steps of purifying and making powders of the optically active hydroxycarboxylic acid monomers.

9. The method of claim 7 wherein a column of LC or HPLC is ion-exchange column or hydrophobic interaction column, and a mobile phase is an acidic solution of which pH is in the range of 1–5.

10. The method of claim 8 wherein the purifying and making powder steps are comprised of the steps of:
   (a) adding strong alkali into the optically active hydroxycarboxylic acids solution and adjusting pH to alkaline range higher than 7;
   (b) removing impurities by organic solvent extraction; and
   (c) drying the purified optically active hydroxycarboxylic acids.

11. The method of claim 1, wherein the monomer is (R)-(–)-3-hydroxybutyric acid and the microorganism is selected from the group consisting of microorganisms of the genus Achromobacter, microorganisms of the genus Acidovorax, microorganisms of the genus Acinetobacter, Actinobacillus sp., Actinomyces sp., *Aeromonas caviae,* microorganisms of the genus Alcaligenes, *Alteromonas macleodii,* microorganisms of the genus Amoebobacter, Aphanocapsa sp., Aphanothece sp., *Aquaspirillum autotrophicum, Azorhizobium caulinodans*, microorganisms of the genus Azospirillum, microorganisms of the genus Azotobacter, microorganisms of the genus Bacillus, microorganisms of the genus Beggiatoa, microorganisms of the genus Beijerinckia, microorganisms of the genus Beneckea, *Bordetella pertussis, Bradyrhizobium japonicum, Caryophanon latum*, microorganisms of the genus Caulobacter, *Chloroflexus aurantiacus*, microorganisms of the genus Chlorogloea, microorganisms of the genus Chromatium, microorganisms of the genus Chromobacterium, microorganisms of the genus Clostridium, microorganisms of the genus Comamonas, microorganisms of the genus Corynebacterium, microorganisms of the genus Derxia, *Desulfococcus multivorans*, microorganisms of the genus Desulfonema, *Desulfosarcina variabilis*, microorganisms of the genus Desulfovibrio, microorganisms of the genus Ectothiorhodospira, *Ferrobacillus ferrooxidans*, Flavobacterium sp., *Haemophilus influenzae*, microorganisms of the genus Halobacterium, *Haloferax mediterranei, Hydroclathratus clathratus, Hydrogenomonas facilis*, microorganisms of the genus Hydrogenophaga, microorganisms of the genus Hyphomicrobium, *Ilyobacter delafieldii, Labrys monachus*, microorganisms of the genus Lactobacillus, microorganisms of the genus Lactococcus, *Lamprocystis roseopersicina, Lampropedia hyalina*, Legionella sp., *Leptothrix discophorus*, microorganisms of the genus Methylobacterium, *Methylococcus thermophilus, Methylocystis parvus, Methylomonas methanica*, microorganisms of the genus Methylosinus, *Methylovibrio soehngenii*, microorganisms of the genus Micrococcus, microorganisms of the genus Microcoleus, microorganisms of the genus Microcystis, microorganisms of the genus Moraxella, microorganisms of the genus Mycobacterium, *Mycoplana rubra*, microorganisms of the genus Nitrobacter, microorganisms of the genus Nitrococcus, microorganisms of the genus Nocardia, *Oscillatoria limosa, Paracoccus dentrificans, Pediococcus halophilus, Penicillium cyclopium*, microorganisms of the genus Photobacterium, *Physarum polycephalum, Protomonas extorquens, Ralstonia eutropha*, microorganisms of the genus Rhizobium, microorganisms of the genus Rhodobacillus, microorganisms of the genus Rhodobacter, microorganisms of the genus Rhodococcus, microorganisms of the genus Rhodocyclus, *Rhodomicrobium vannielii*, microorganisms of the genus Rhodopseudomonas, microorganisms of the genus Rhodospirillum, *Sphaerotilus natans, Sphingomonas paucimobilis;* microorganisms of the genus Spirillum, microorganisms of the genus Spirulina, microorganisms of the genus Staphylococcus, microorganisms of the genus Stella, *Streptococcus thermophilus*, microorganisms of the genus Streptomyces, microorganisms of the genus Synechococcus, *Syntrophomonas wolfei*, microorganisms of the genus Thiobacillus, microorganisms of the genus Thiocapsa, *Thiocystis violacea*, microorganisms of the genus Thiodictyon, *Thiosphaera pantotropha, Trichodesmimum thiebautii, Vibrio parahaemolyticus, Xanthobacter autotrophicus, Xanthomonas maltophilia* and microorganisms of the genus Zoogloea; and (b) preparing (R)-(−)-3-hydroxybutyric acid by auto-degradation of PHB accumulated in the above cultured microorganism by keeping the cultured microorganism in a degradation solution.

12. The method of claim 11 wherein the microorganism is selected from the group consisting of microorganisms of *Alcaligenes latus*, Bacillus sp., Corynebacterium sp., *Methylosinus trichosporium, Rhodospirillum rubrum* and *Ralstonia eutropha*.

13. The method of claim 1, wherein the monomers are monomers of (R)-(−)-3-hydroxybutyic acid and 4-hydroxybutyric acid and the polyhydroxyalkanoate is poly-3-hydroxybutyrate-co-4-hydroxybutyrate.

14. The method of claim 13 wherein said microorganism is *Alcaligenes latus*.

15. The method of claim 1 wherein the monomers are monomers of (R)-(−)-3-hydroxybutyic acid and (R)-(−)-3-hydroxyvaleric acid, and the polyhydroxyalkanoate is poly-3-hydroxybutyrate-co-3-hydroxyvalerate.

16. The method of claim 15 wherein said microorganism is *Ralstonia eutropha*.

17. The method of claim 1, wherein said microorganism is recombinant microorganism.

18. The method of claim 17, wherein said recombinant microorganism is *Ralstonia eutropha* containing Ralstonia eutropha PHA biosynthesis genes.

\* \* \* \* \*